(12) United States Patent
Forte et al.

(10) Patent No.: US 8,252,338 B2
(45) Date of Patent: Aug. 28, 2012

(54) SYNTHETIC LDL AS TARGETED DRUG DELIVERY VEHICLE

(75) Inventors: Trudy M. Forte, Berkeley, CA (US); Mina Nikanjam, Richmond, CA (US)

(73) Assignees: The Regents of the University of California, Oakland, CA (US); Children's Hospital & Research Center Oakland, Oakland, CA (US)

( * ) Notice: Subject to any disclaimer, the term of this patent is extended or adjusted under 35 U.S.C. 154(b) by 605 days.

(21) Appl. No.: 12/084,845

(22) PCT Filed: Nov. 13, 2006

(86) PCT No.: PCT/US2006/044163
§ 371 (c)(1),
(2), (4) Date: Sep. 22, 2009

(87) PCT Pub. No.: WO2007/145659
PCT Pub. Date: Dec. 21, 2007

(65) Prior Publication Data
US 2010/0047163 A1    Feb. 25, 2010

Related U.S. Application Data

(60) Provisional application No. 60/735,575, filed on Nov. 10, 2005.

(51) Int. Cl.
*A61K 9/14* (2006.01)
*A61K 38/04* (2006.01)
*A61K 38/16* (2006.01)
*C07K 7/00* (2006.01)
*C07K 14/00* (2006.01)

(52) U.S. Cl. ....... 424/499; 514/1.2; 514/17.7; 514/19.3; 514/21.3; 514/21.4; 514/21.6; 530/324; 530/326; 530/328; 977/795; 977/799; 977/801; 977/906

(58) Field of Classification Search .................. None
See application file for complete search history.

(56) References Cited

U.S. PATENT DOCUMENTS 6,670,452 B2 * 12/2003 Halbert et al. ................ 530/359
7,220,833 B2 *  5/2007 Nelson et al. ................ 530/350
2005/0100986 A1  5/2005 Verma et al.

FOREIGN PATENT DOCUMENTS

WO        WO 8702061 A  *  4/1987

OTHER PUBLICATIONS

Baillie, G. et al. "A synthetic low density lipoprotein particle capable of supporting U937 proliferation in vitro." Journal of Lipid Research, 2002, vol. 43, pp. 69-73.

* cited by examiner

*Primary Examiner* — Jeffrey E Russel
(74) *Attorney, Agent, or Firm* — Kilpatrick Townsend & Stockton LLP

(57) ABSTRACT

The present invention provides a synthetic LDL nanoparticle comprising a lipid moiety and a synthetic chimeric peptide so as to be capable of binding the LDL receptor. The synthetic LDL nanoparticle of the present invention is capable of incorporating and targeting therapeutics to cells expressing the LDL receptor for diseases associated with the expression of the LDL receptor such as central nervous system diseases. The invention further provides methods of using such synthetic LDL nanoparticles.

26 Claims, 24 Drawing Sheets

A

B

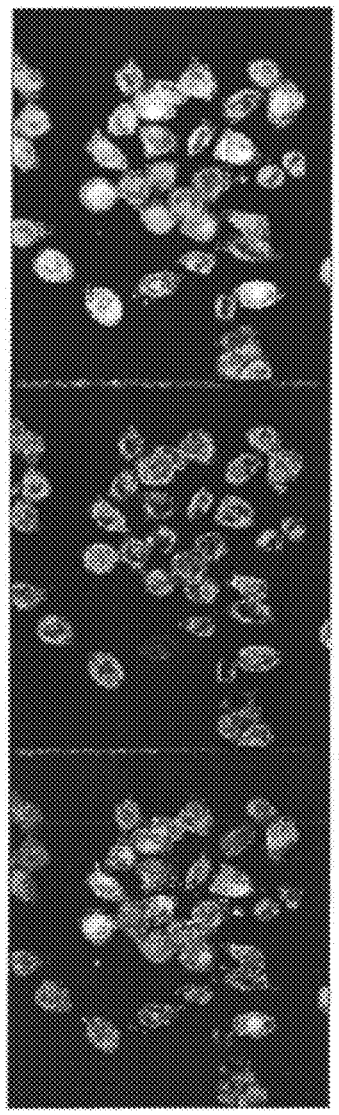

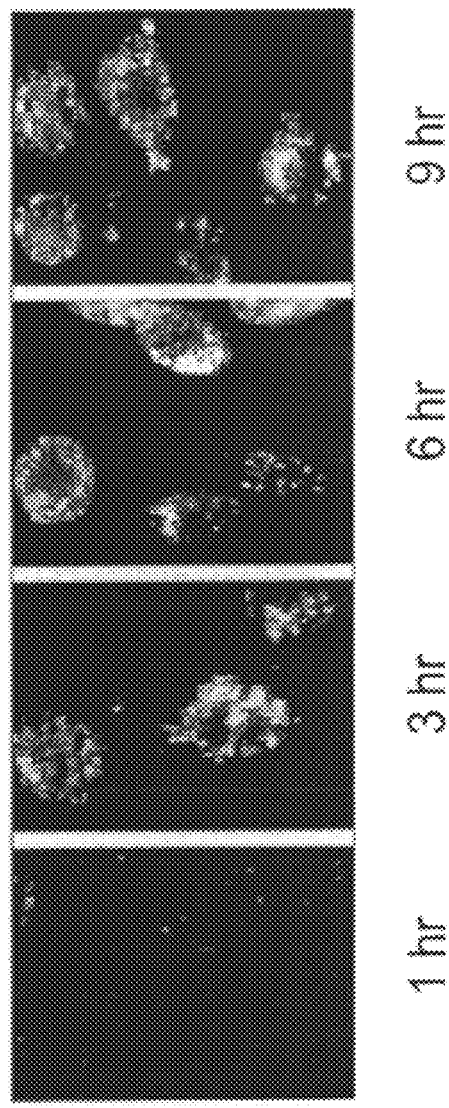

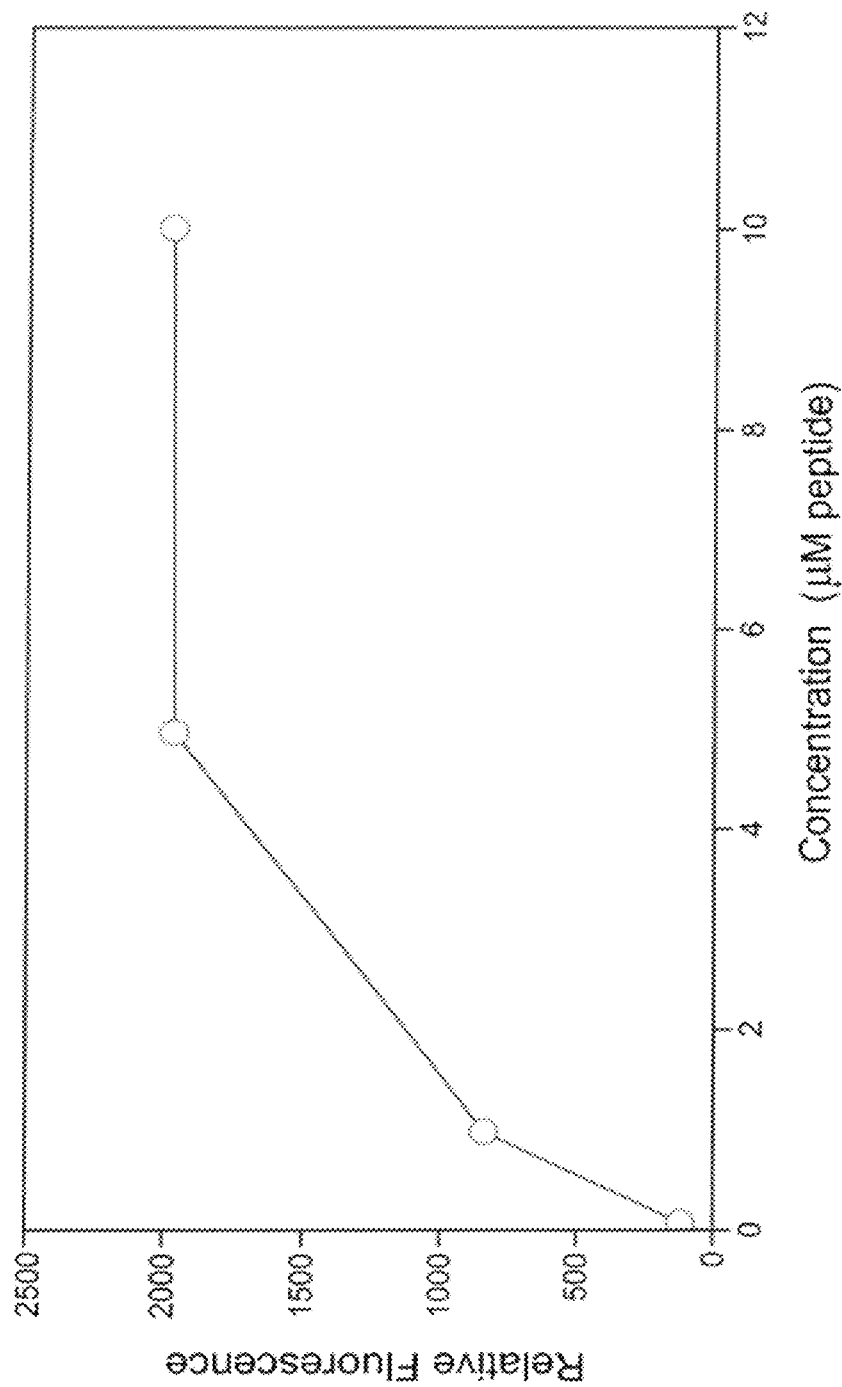

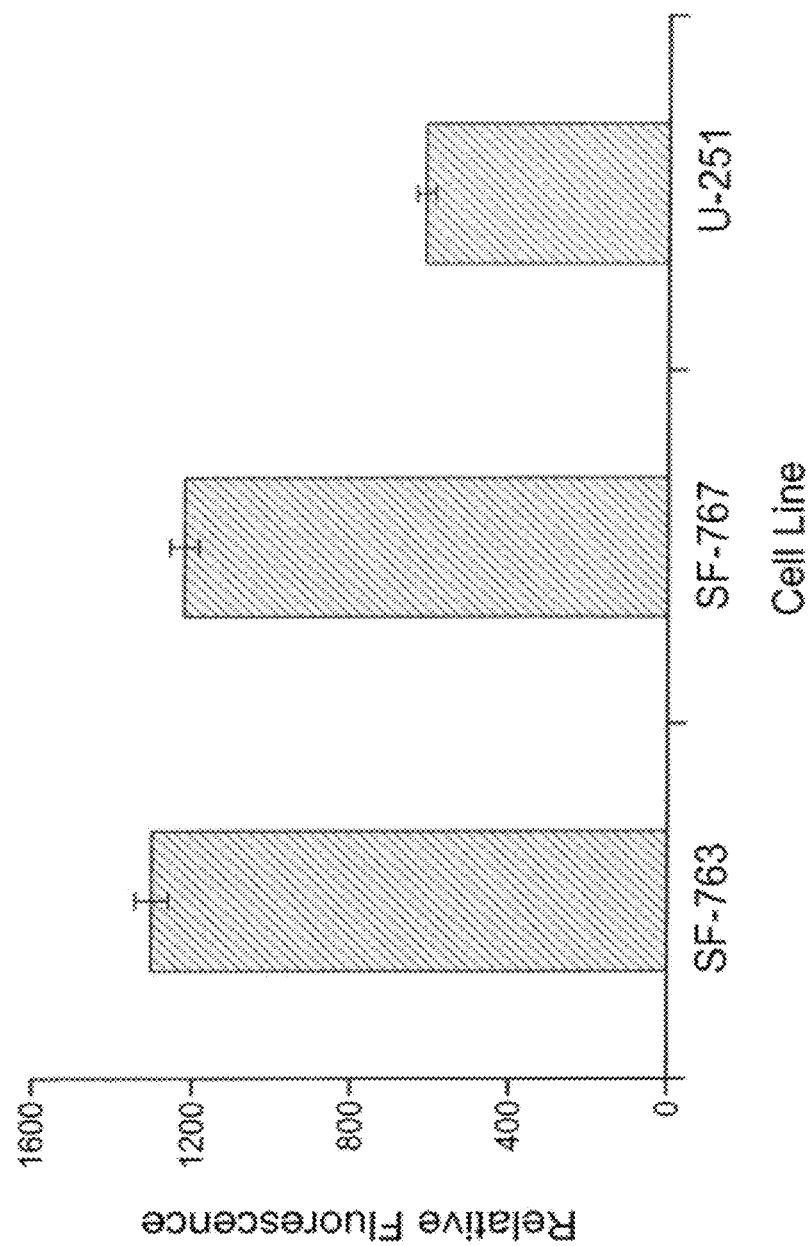

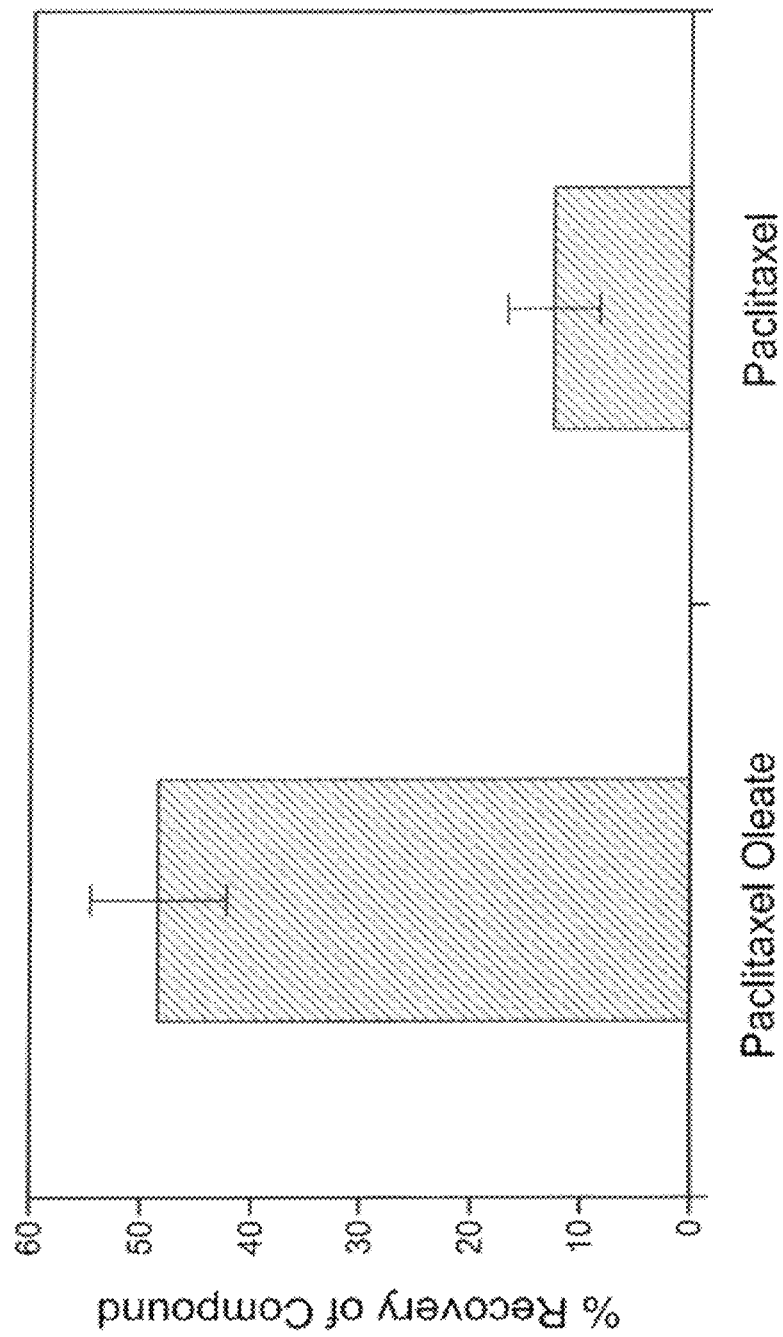

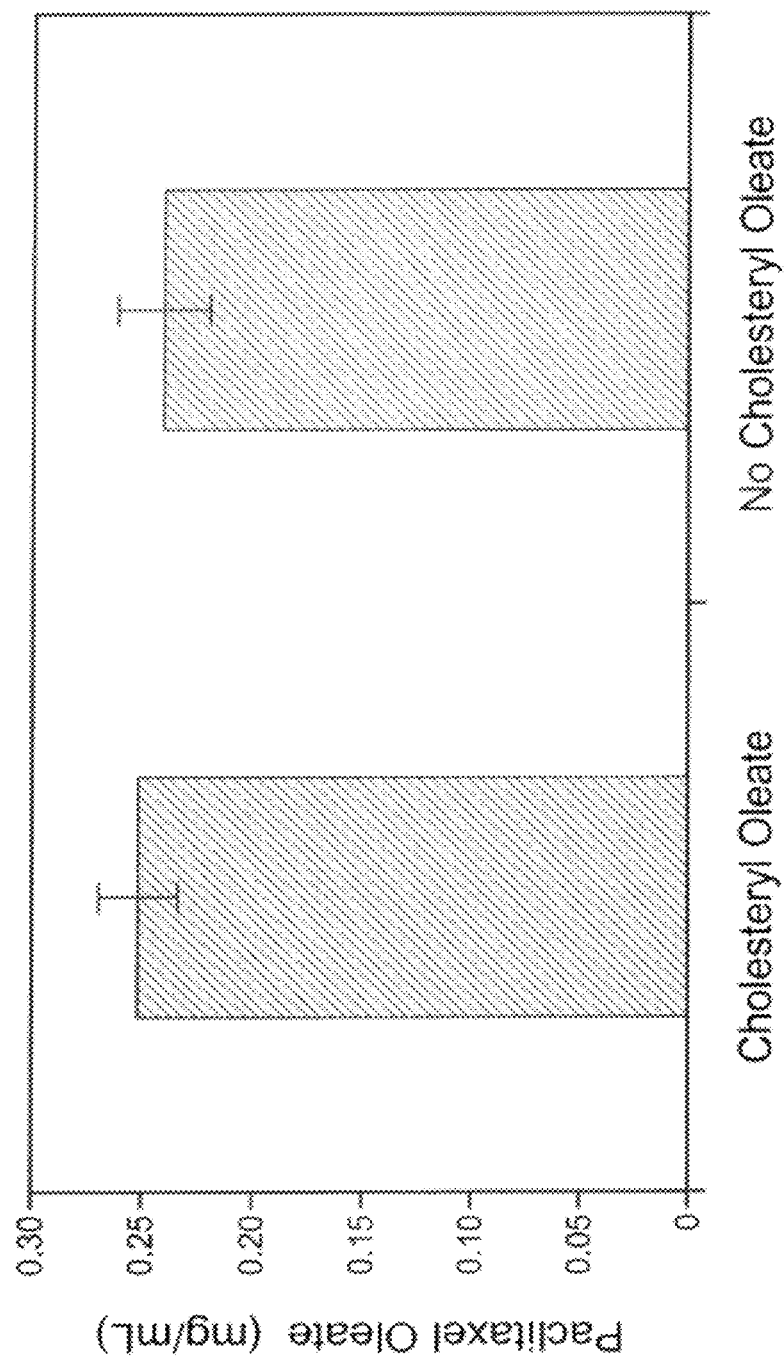

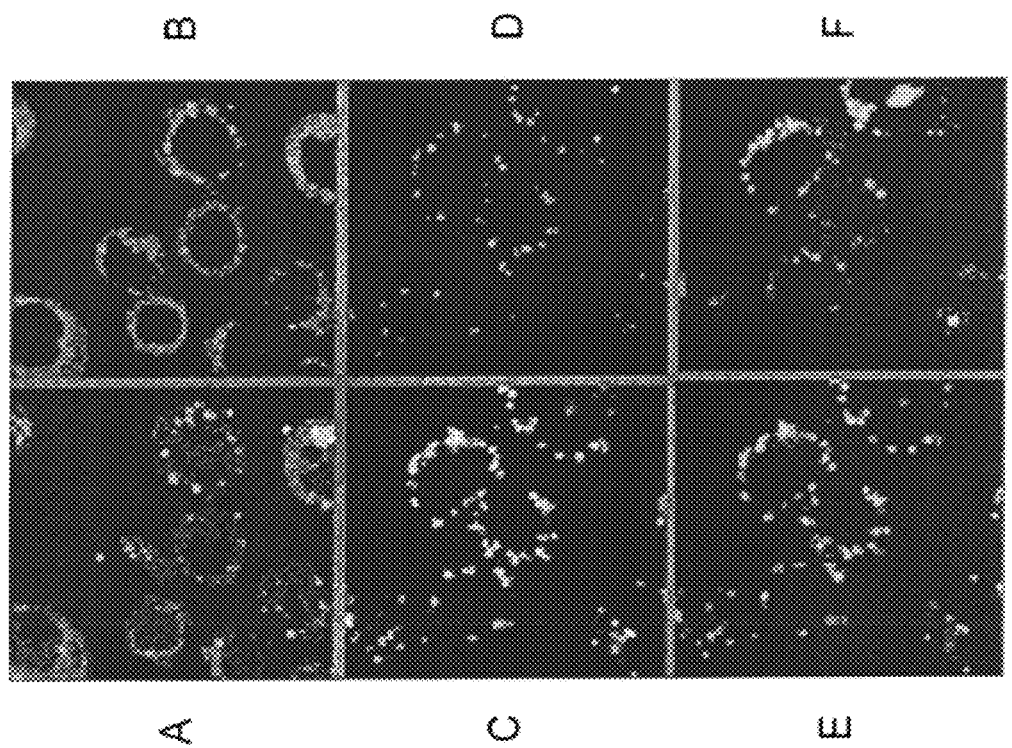

SYNTHETIC LDL AS TARGETED DRUG DELIVERY VEHICLE

CROSS-REFERENCES TO RELATED APPLICATIONS

This application claims priority to U.S. Application No. 60/735,575 filed on Nov. 10, 2005, which is incorporated herein by reference.

STATEMENT AS TO RIGHTS TO INVENTIONS MADE UNDER FEDERALLY SPONSORED RESEARCH OR DEVELOPMENT

This invention was made during work supported in part by the U.S. Department of Energy under Contract No. DE-AC02-05CH11231. The government has certain rights in this invention.

BACKGROUND OF THE INVENTION

The blood-brain barrier (BBB) is a specialized physical and enzymatic barrier that segregates the brain from systemic circulation. The physical portion of the BBB is composed of endothelial cells arranged in a complex system of tight junctions which inhibit any significant paracellular transport.

The BBB functions as a diffusion restraint selectively discriminating against substance transcytosis based on lipid solubility, molecular size and charge thus posing a problem for drug delivery to the brain. Drug delivery across the BBB is further problematic due to the presence of a high concentration of drug efflux transporters (e.g., P-glycoprotein, multi-drug resistant protein, breast cancer resistant protein). These transporters actively remove drug molecules from the endothelial cytoplasm before they even cross into the brain.

The methods that are currently employed for drug delivery in treatment of brain diseases are generally non-specific, inefficient, complex to perform and very expensive.

An additional problem to consider when treating brain diseases is the diffusion of the drug on its vehicle across the tumor or affected tissue. Mostly the size, as well as other physiologic characteristics of the vehicles that are currently in use for such delivery of drugs to the brain, hamper efficient diffusion of the drug through the diseased tissue. The lack of efficient drug diffusion affects the efficacy of the treatment.

Peptides have been extensively studied as carrier molecules for drug delivery to the brain in hope they could be employed as drug delivery vehicles. Peptides, are, however, problematic due to their limited bioavailability. Even though methods to increase the bioavailability of such molecules have been intensively explored, they resulted in modest success at best.

Largely due to the strict regulation of molecular transport across the BBB and lack of success with currently available drug administration methods, a growing number of brain disorders, particularly cancers, remain treated inefficiently or not treated at all. There is currently a need for specific, less invasive and more efficient methods of drug delivery to the brain for the ever growing number of brain illnesses, particularly brain cancers.

Increased cell proliferation and growth is a trademark of cancer. The increase in cellular proliferation is associated with high turnover of cell cholesterol. Cells requiring cholesterol for membrane synthesis and growth may acquire cholesterol by receptor mediated endocytosis of plasma low density lipoproteins (LDL) (Brown, M. S. et al., *Science* 232:34-47 (1986)), the major transporter of cholesterol in the blood, or by de novo synthesis. LDL is taken up into cells by a receptor known as the LDL receptor (LDLR); the LDL along with the receptor is endocytosed and transported into the cells in endosomes. The endosomes become acidified and this releases the LDL receptor from the LDL; the LDL receptor recycles to the surface where it can participate in additional uptake of LDL particles (Maletinska, L. et al., *Cancer Res* 60:2300-2303 (2000)).

There is a body of evidence that suggests that tumors in a variety of tissues have a high requirement for LDL to the extent that plasma LDLs are depleted. The increased import of LDL into cancerous cells is thought to be due to elevated LDL receptors (LDLR) in these tumors. Some tumors known to express high numbers of LDLRs include some forms of leukemia (Vitols, S. et al, *Blood* 63:1186-1193 (1984); Vitols, S. et al., *Lancet* 2:1150-1153 (1985), 9), lung tumors (Vitols, S. et al., *Cancer Res* 52:6244-6247 (1992); Lundberg, B. *Cancer Res* 47:4105-4108 (1987)), colorectal tumors (Lum, D. F. et al., *Int J Cancer* 83:162-166 (1999)) and ovarian cancer (Avall-Lundqvist, E. H. et al., *Acta Oncol* 35:1007-1010 (1996)).

Comparative studies of normal and malignant brain tissues have shown a high propensity of LDLRs to be associated with malignant and/or rapidly growing brain cells and tissues. Using immunohistochemistry, Pitas et al. (Pitas, R. E. et al., *J Biol Chem* 262:14352-14360 (1987)) examined monkey and rat brain and reported relatively few LDLRs in normal neurons and glial cells. Limited staining for LDLR was shown in astrocytes abutting the arachnoid space and in astrocytes in the white matter. However, large numbers of high affinity LDLR have been reported for the rapidly proliferating primary glial cells isolated from 1-2 day old rat pups (Jung-Testas, I. et al., *J Steroid Biochem Molec Biol* 42:597-605 (1992)). These findings strongly suggest that rapidly growing brain cells such as those seen in early development and in aggressively growing brain tumors exhibit increased expression of LDLRs due to their increased requirement for cholesterol.

Additional in vivo studies showed that LDLRs do appear in brain malignancies. Leppala et al. (Leppala, J. et al., *Br J Cancer* 71:383-387 (1995)) used PET imaging, and demonstrated that $^{99m}$Tc-LDL localizes in human brain tumors in vivo but not in normal brain.

Although the major transporter of cholesterol into cells and tissues, LDL is excluded from performing this function in the brain being too large to cross the blood brain barrier.

The LDLR ligand is apoB100, a 514 kDa glycoprotein on the surface of LDL. This lipid binding protein is very large (~500 kD) and consists of hydrophobic domains, amphipathic beta sheets and amphipathic helices; unlike other apolipoproteins it is not an exchangeable protein. The protein is highly insoluble in aqueous medium and has a propensity to aggregate thus making it a difficult protein with which to work. The structure of apoB100 is now well defined (Segrest J. P. et al., *J Lipid Res* 42:1346-1367 (2001)). Early work of Yang et al. (Yang C.-Y. et al., *Nature* 323:738-742 (1986)) suggested that the apoB sequence between a.a. 3345-3381 contains the LDLR binding domain. Indeed, Yang et al. showed that a synthetic peptide corresponding to this region can bind to human skin fibroblasts and regulate HMG-CoA reductase. Law and Scott (Law A. et al., *J Lipid Res* 31:1109-1120 (1990)), using cross-species comparisons, further refined the binding domain to a nine amino acid segment consisting of residues 3359-3367. The results of these studies were further confirmed by site directed mutagenesis studies of Boren et al. (Boren, J. et al., *J Clin Invest* 101:1084-1093

(1998)) who showed that apoB100 protein with mutations in this region lacked the ability to interact with the LDLR.

Even though human cerebral spinal fluid (CSF) contains apolipoproteins including apoE, apoA-I, apoC-III and C-II (Roheim, P. S. et al., *Proc Natl Acad Sci USA* 76:4646-4649 (1979)) thus making a case for lipid transport in the brain and cholesterol homeostasis similar to that of other tissues, apoB100 was not detected in the CSF consistent with the exclusion of LDL by the blood brain barrier. CSF lipoprotein particles examined by electron microscopy were in the size range of 11-13 nm.

Among the problematic and inefficiently treated brain cancer is glioblastoma multiforme (GBM). This devastating brain tumor is 100% fatal. Moreover, over 85% of total primary brain cancer-related deaths are due to GBM. Current therapies rely on a multimodal approach including neurosurgery, radiation therapy and chemotherapy. Even the best efforts using these approaches have resulted in only a modest increase in survival time for patients afflicted with this tumor.

GBM being gliomas of the highest malignancy are characterized by uncontrolled, aggressive cell proliferation and general resistance to conventional therapies. GBM cells in culture have high numbers of low density lipoprotein receptors (LDLR) (Maletinska, L. et al., *Cancer Res* 60:2300-2303 (2000)). Since this receptor is nearly absent in neuronal cells and normal glial cells, it represents an ideal target for the delivery of therapeutic agents such as cytotoxins or radiopharmaceuticals. Efforts to improve existing therapies or to develop new ones have not been successful and the outcome of treatment for malignant gliomas is only modest, at best, with a median survival time of approximately 10 months (Miller, P. J. et al., *Int J Radiat Oncol Biol Phys* 19:275-280 (1990); Shibamoto, Y. et al., *Radiother Oncol* 18:9-17 (1990); Barker, F. G. 2$^{nd}$ et al., *Neurosurgery* 42:981-987, (1998)).

Unlike normal brain cells that have few LDL receptors, GBM cells in culture have high numbers of LDL receptors on their surface (Brown, M. S. et al., *Science* 232:34-47 (1986)). Other brain cancers are likely to also have high expression of LDLR due to the highly proliferative nature of the cancerous tissue and need for cholesterol turnover.

This suggests that the LDL receptor is a potential unique molecular target in GBM and other brain malignancies for the delivery of anti-tumor drugs via LDL particles.

The present invention addresses the need of targeted delivery of therapeutic compounds to cancers and other diseases where the LDLR is presented on the cell surface via a synthetically synthesized LDL nanoparticle capable of carrying and transporting therapeutics.

BRIEF SUMMARY OF THE INVENTION

The present invention provides a novel synthetic LDL (sLDL) nanoparticle comprising a lipid moiety and a synthetic chimeric peptide wherein the lipid moiety forms a particle of about 10 to about 30 nm in size and the synthetic chimeric peptide comprises an amphipathic α-helix and an LDL receptor binding domain consisting of the following sequence:

(R$^1$)$_x$-Arg-Leu-Thr-Arg-Lys-Arg-Gly-Leu-Lys-(R$^2$)$_y$ in which
R$^1$ is an amino acid sequence from 1 to 40 amino acids wherein each amino acid is independently selected from the group consisting of naturally occurring amino acids and amino acid mimetics;
R$^2$ is an amino acid sequence from 1 to 40 amino acids wherein each amino acid is independently selected from the group consisting of naturally occuring amino acids and amino acid mimetics; and
x and y are independently selected and are equal to zero or one (SEQ ID NO:9).

In some embodiments, x and y are both zero (SEQ ID NO:1).

In some other embodiments, x is one;
R$^1$ is Asp-Trp-Leu-Lys-Ala-Phe-Tyr-Asp-Lys-Val-Ala-Glu-Lys-Leu-Lys-Glu-Ala-Phe (SEQ ID NO:2); y is one; and R$^2$ is Leu-Ala.

In yet other embodiments, x is one;
R$^1$ is Asp-Trp-Phe-Lys-Ala-Phe-Tyr-Asp-Lys-Val-Ala-Glu-Lys-Phe-Lys-Glu-Ala-Phe (SEQ ID NO:10); y is one; and R$^2$ is Leu-Ala.

In some other embodiments, x is one; R$^1$ is Tyr-Lys-Leu-Glu-Gly-Thr-Thr (SEQ ID NO:11); y is one; and R$^2$ is Leu-Ala-Thr-Ala-Leu-Ser (SEQ ID NO:12).

In some embodiments, x is one;
R$^1$ is Pro-Ala-Leu-Glu-Asp-Leu-Arg-Gln-Gly-Leu-Leu-Pro (SEQ ID NO:13); y is one; and R$^2$ is Leu.

In other embodiments, x is one;
R$^1$ is Asp-Trp-Leu-Lys-Ala-Phe-Tyr-Asp-Lys-Val-Ala-Glu-Lys-Leu-Lys-Glu-Ala-Phe-Pro (SEQ ID NO:14); y is one; and
R$^2$ is Pro-Asp-Trp-Leu-Lys-Ala-Phe-Tyr-Asp-Lys-Val-Ala-Glu-Lys-Leu-Lys-Glu-Ala-Phe (SEQ ID NO:15).

In other embodiments, x is one;
R$^1$ is Asp-Trp-Leu-Lys-Ala-Phe-Tyr-Asp-Lys-Val-Ala-Glu-Lys-Leu-Lys-Glu-Ala-Phe-Tyr-Lys-Leu-Glu-Gly-Thr-Thr (SEQ ID NO:16); y is one; and R$^2$ is Leu-Ala-Thr-Ala-Leu-Ser (SEQ ID NO:12).

In some embodiments of the present invention, the synthetic LDL nanoparticle is 10 to 20 nm in size. In some embodiments, the sLDL nanoparticle is 10 nm in size. In some other embodiments, the LDL nanoparticle is 20 nm in size.

In some embodiments, the lipid moiety of the sLDL nanoparticle comprises a microemulsion of lipids selected from the group consisting of phospholipids, triglyceride, cholesteryl ester and a combination thereof. In some embodiments, cholesteryl ester is omitted from the lipid moiety.

In some embodiments, the microemulsion comprises phospholipids, triolein and cholesteryl oleate.

In some embodiments the ratio of phospholipids:triolein:cholesteryl oleate in the microemulsion is 3:1:2. In some other embodiments, the ratio of phospholipids:triolein:cholesteryl oleate in the microemulsion is 3:0.5:2. In other embodiments, the ratio of phospholipids:triolein:cholesteryl oleate in the microemulsion is 3:2:0.

In some embodiments, the amphipathic α-helix of the sLDL nanoparticle comprises 10 to 22 amino acids.

In some embodiments, the amphipathic α-helix of the sLDL nanoparticle is selected from the group consisting of Segrest peptide, ApoAI helix 9, ApoAI helix 10; and 18A peptide substituted with F3 and F4.

In some embodiment, the sLDL nanoparticle further comprises a therapeutic compound. In some embodiments, the therapeutic compound is selected from the group consisting of small organic molecules, radioisotopes, inorganic molecules, polypeptides, peptides, siRNA, antibodies, nucleic acids, and bacterial toxins and a combination thereof.

In some embodiments, the therapeutic compound is selected from the group consisting of small organic molecules, inorganic molecules, therapeutic peptides and proteins, antibodies, radioisotopes, siRNA and nucleic acids for gene therapy, toxins such as anthrax toxin, shiga toxin, A chain of diphtheria toxin, *Pseudomonas* exotoxin A, and known anti-cancer agents such as taxol, paclitaxel oleate, paclitaxel, and doxirubucin.

In some embodiments, the therapeutic compound is taken up by the lipid moiety of the synthetic LDL nanoparticle or covalently or non-covalently attached to the amphipathic α-helix of the chimeric peptide.

In some embodiments, the sLDL nanoparticle of the present invention is administered to treat or prevent a disease. In some embodiments, the disease is cancer. In some embodiments, the disease is any disease where the diseased cells express the LDL receptor (LDLR).

In some embodiments the cancer treated or prevented by the sLDL nanoparticle of the present invention is selected from the group consisting of carcinomas, sarcomas, adenocarcinomas, lymphomas, leukemias, etc., including solid and lymphoid cancers, kidney, breast, lung, bladder, colon, ovarian, prostate, pancreas, stomach, brain, head and neck, skin, uterine, testicular, glioma, esophagus, and liver cancer, including hepatocarcinoma, lymphoma, including B-acute lymphoblastic lymphoma, non-Hodgkin's lymphomas (e.g., Burkitt's, Small Cell, and Large Cell lymphomas) and Hodgkin's lymphoma, leukemia (including AML, ALL, and CML), multiple myeloma, mantle cell lymphoma, Waldenstrom's macrogobulinemia, and Philadelphia positive cancers.

In some embodiments, the sLDL nanoparticle of the present invention is used to treat or prevent brain disease. In some embodiments, the brain disease is brain cancer. In some embodiments, the brain cancer is selected from the group consisting of GBM, astrocytoma, ependymoma, medulloblastoma, oligodendrocytoma, meningioma, pituitary adenoma, meurilemmona, metastatic carcinoma, craniopharyngioma and dermoid, epidermoid, or teratoma, angiomas and vascular malformations, sarcomas, pinealoma, chrodoma, and granuloma.

In some embodiments, the sLDL nanoparticle of the present invention is used to treat diseases of the central nervous system. In some embodiments, the disease of the central nervous system is selected from the group consisting of stroke, epilepsy, head trauma, viral infection (e.g., HIV-associated cognitive dysfunction, meningitis caused by picomavirus, togavirus, herpesvirus paramyxovirus, and areanavirus), bacterial infection (e.g., meningitis such as cryptococcal meningitis and fulminant bacterial meningitis, neurotuberculosis, toxoplasmosis, and neurosyphilis), fungal, rickettsial, protozoan, or helminthic infections, Alzheimer's disease, Parkinson's disease, multiple sclerosis, and hereditary metabolic diseases of the brain.

In some embodiments the sLDL nanoparticle of the present invention is administered to the patient systemically.

In some embodiments, the sLDL nanoparticle is administered locally. In some embodiments, wherein the sLDL nanoparticle is used to treat or prevent brain disease, the sLDL nanoparticle is administered to the patient using convection enhanced delivery.

BRIEF DESCRIPTION OF THE DRAWINGS

FIG. 1. B depicts a 400× micrograph of a biopsy specimen from a patient with GBM. The darker colored cells are positive for the LDLR and are heavily labeled.

FIG. 3. B depicts a cartoon of the synthetic LDL nanoparticle (sLDL). As shown, the hydrophobic core of the particle consists of triglyceride (TG) and cholesteryl ester (CE) which is stabilized by phospholipids and the numerous copies of synthetic peptide.

FIG. 10 depicts colocalization of fluorescently labeled (FITC) peptide and fluorescently labeled lipid (DiI). SF-767 cells were incubated with sLDL that were dual labeled (6 hr, 37° C., 15 μM peptide). Cells were viewed live, and Hoescht stain (blue) was used for nuclear staining. The merged image indicates that peptide and lipid co-localize in cells. This suggests that sLDL particles remain intact upon entry into the cell.

FIG. 11. A uses fluorescence microscopy to show that uptake of DiI-labeled synthetic LDL is time dependent. Uptake of DiI-labeled lipids was tested at 1, 3, 6 and 9 hours. SF-767 cells were fixed with 4% paraformaldehyde at each time point prior to microscopy. The experiment was repeated with separately produced batch of synthetic LDL and yielded identical results. FIG. 11. B depicts FACS analysis the data of which indicate that uptake of DiO-labeled synthetic LDL is time-dependent. SF-767 cells were incubated for 1, 3, 6, and 9 hours at 37° C. with the synthetic LDL particles previously labeled with DiO. Data represents mean+/−standard deviation of three separate wells. FIG. 11. C depicts the results of FACS analysis showing that uptake of DiO-labeled synthetic LDL particles is concentration dependent. Cells were incubated for 3 hours at 37° C. with varying concentrations of synthetic LDL particles (0.1, 1, 5 and 10 µM peptide) that had been previously labeled with DiO. Data represents mean+/−standard deviation of three separate wells. This experiment was repeated two additional times with separate synthetic LDL batches and yielded identical results.

FIG. 12 depicts that the uptake of DiO-labeled synthetic LDL is dependent on receptor number. Cells were incubated for 3 hours at 37° C. with synthetic LDL (1.5 µM peptide) previously labeled with DiO. At the conclusion of the experiment, cells were trypsinized and resuspended in PBS. Data for each cell line represents the mean+/−standard deviation of three separate wells. This experiment was repeated using a separate batch of synthetic LDL and yielded similar results.

FIG. 14 depicts a comparison of paclitaxel oleate and paclitaxel incorporation into microemulsions. FIG. 14. A depicts that Paclitaxel oleate demonstrates significantly greater incorporation into a lipid microemulsion than paclitaxel. FIG. 14. B depicts that Paclitaxel oleate incorporation into microemulsion is not affected by the presence of cholesteryl oleate. Equimolar amounts of paclitaxel and paclitaxel oleate were added to each initial lipid mixture. Paclitaxel oleate and paclitaxel amounts were quantified by reversed phase HPLC. Each data point represents the mean+/−standard deviation of three separate microemulsions.

FIG. 15. B depicts that Paclitaxel oleate incorporation in a microemulsion is not affected by the addition of the peptide. Paclitaxel oleate amounts were quantified by reversed phase HPLC. Each data point represents the mean+/−standard deviation of three separate microemulsions.

FIG. 20 depicts confocal microscopy of SF-767 cells revealing co-localization of peptide and lipid in lysosomes. The representative images in FIG. 20 A and FIG. 20 B were obtained from cells fixed after 3 hours incubation of cells with dual labeled sLDL nanoparticles (1.5 µM peptide) where the peptide carried the FITC label and lipid the DiI label. FIG. 20 A depicts FITC label of peptide and FIG. 20 B depicts DiI label in lipids. The representative images in FIG. 20 C through F were obtained from living SF-767 cells after 1 hour incubation with dual labeled sLDL nanoparticle (1.5 µM peptide). FIG. 20 C depicts FITC-labeled peptide; FIG. 20 D depicts DiI-labeled lipids; FIG. 20 E depicts images in C and D merged to show co-localization of peptide and lipid; FIG. 20 F depicts Lysotracker Blue image for localization of lysosome revealing co-localization of the peptide and lipid in lysosomes.

BRIEF DESCRIPTION OF THE SEQUENCES

Figure 1:
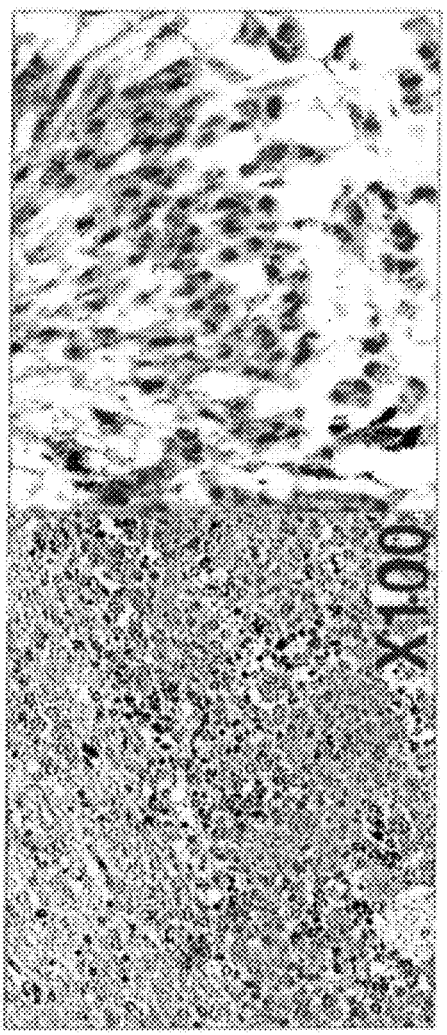
FIG. 1. A depicts a micrograph of a section of athymic rat implanted with human glioblastoma multiforme U-251 MG cells and stained for LDLR by use of LDLR antibody. The clearer field in the upper left quadrant is the normal rat brain tissue. The tumor boundary forms a diagonal across the field with heavily labeled anti-LDL receptor tumor cells interspersed with some unlabeled tumor cells.

SEQ ID NO:1 is the 9 amino acid ApoB100 LDLR-binding domain.
SEQ ID NO:2 is the 18A Segrest peptide.
SEQ ID NO:3 is the 18A Chimeric peptide.
SEQ ID NO:4 is the 4F 18PA peptide (F3, F4).
SEQ ID NO:5 is the B-peptide.
SEQ ID NO:6 is the ApoA-1 helix 9 (11-A) chimeric peptide.
SEQ ID NO:7 is the 18A-P-LDLR-P-18A chimeric peptide.
SEQ ID NO:8 is the 18A-LDLR chimeric peptide including the LDLR flanking sequences.

DETAILED DESCRIPTION OF THE INVENTION

I. Introduction

The present invention is based on the surprising discovery that a novel synthetic low density lipoprotein (sLDL) nanoparticle comprising a lipophilic α-helix with the apoB100 minimal sequence that recognizes the LDL receptor (LDLR) can be used to specifically bind to tumors overexpressing LDLR. Furthermore, the sLDL nanoparticle of the present invention has the physiological and chemical characteristics that are ideal for specific and targeted delivery of drugs to cancers or other diseases where the LDLR is expressed.

The novel sLDL nanoparticle of the present invention is highly reproducible in size and composition, is recognized and internalized by glioblastoma mutliforme (GBM) cells in vitro and can be delivered for distribution in vivo. The synthetic LDL nanoparticle of the present invention avidly binds its constituent peptide components and is specific for the LDLR. Furthermore the sLDL nanoparticle of the present invention exhibits a greater diffusion in a tumor than native LDL and is thus more efficacious in the delivery of drugs to cancers of the central nervous system including glioblastoma multiforme (GBM).

There is a current need for generating novel carriers capable of delivery of therapeutics into tumors. Using the LDLR as a target, we have developed a system in which synthetic LDL nanoparticles represent an efficient mechanism for drug delivery. The sLDL nanoparticles of the present invention are recognized by and interact with the LDLR, thus making the sLDL nanoparticles ideal candidates for not only efficient but also specific delivery of therapeutics to cancers and other diseased tissues overexpressing the LDLR. For example, glioblastoma multiforme, a highly aggressive brain cancer with low likelihood of success with currently available treatments, overexpresses the LDLR and can thus be targeted with the sLDL nanoparticle of the present invention. Being a small particle, the sLDL nanoparticle, can more readily diffuse into the tumor mass than native LDL.

The unique aspects of the synthetic LDL nanoparticles are based on their being generated by using chimeric peptides (29 to 46-mer) that represent the fusion of a lipophilic amphipathic α-helix with the apoB100 sequence that recognizes the LDLR. This apoB sequence consists of a unique 9 amino acid residue that recognizes the LDLR.

The sLDL nanoparticles of the present invention are capable of serving as "carriers" for therapeutics and allow for their targeted delivery into the tissue or tumor of interest. sLDL nanoparticles can be used to treat brain cancers such as GBM, astrocytoma, ependymoma, medulloblastoma, oligodendrocytoma, meningioma, pituitary adenoma, meurilemmona, metastatic carcinoma, craniopharyngioma and dermoid, epidermoid, or teratoma, angiomas and vascular malformations, sarcomas, pinealoma, chrodoma, and granuloma. sLDL nanoparticles can also be used to deliver therapeutic agents to the brain to treat other brain diseases, including but not limited to stroke, epilepsy, head trauma, viral infection (e.g., HIV-associated cognitive dysfunction, meningitis caused by picornavirus, togavirus, herpesvirus, paramyxovirus, and areanavirus), bacterial infection (e.g., meningitis such as cryptococcal meningitis and fulminant bacterial meningitis, neurotuberculosis, toxoplasmosis, and neurosyphilis), fungal, rickettsial, protozoan, or helminthic infections, Alzheimer's disease, Parkinson's disease, multiple sclerosis, and hereditary metabolic diseases of the brain. Furthermore, the sLDL nanoparticles of the present invention can be used to deliver therapeutic agents to any tissue expressing the LDLR.

The sLDL nanoparticles of the present invention, can be used as "carriers" for a number of drugs and can thus be used to treat other human cancers. Examples of such cancers include but are not limited to carcinomas, sarcomas, adenocarcinomas, lymphomas, leukemias, etc., including solid and lymphoid cancers, kidney, breast, lung, bladder, colon, ovarian, prostate, pancreas, stomach, brain, head and neck, skin, uterine, testicular, glioma, esophagus, and liver cancer, including hepatocarcinoma, lymphoma, including B-acute lymphoblastic lymphoma, non-Hodgkin's lymphomas (e.g., Burkitt's, Small Cell, and Large Cell lymphomas) and Hodgkin's lymphoma, leukemia (including AML, ALL, and CML), multiple myeloma, mantle cell lymphoma, Waldenstrom's macrobulinemia, and Philadelphia positive cancers.

In some instances, the sLDL nanoparticle, can be administered systemically. Systemic modes of administering therapeutics are well known in the art, e.g., parenterally or intravenously. This is particularly true of administration for cancers and diseases other than diseases of the central nervous system.

In some other instances, the sLDL nanoparticle can be administered locally. For brain tumors, for example, local administration can be aided by convection enhanced delivery. Other methods of local drug administration are well known in the art.

Some therapeutics of choice include, but are not limited to, small organic molecules, inorganic molecules, therapeutic peptides and proteins, antibodies, radioisotopes, siRNA and nucleic acids for gene therapy, toxins such as anthrax toxin, shiga toxin, A chain of diphtheria toxin, *Pseudomonas* exotoxin A, and known anti-cancer agents such as taxol, paclitaxel oleate, paclitaxel, doxirubucin (adriamycin, analogs, and derivatives), camptothecin, irinotecan, SN-38, nitrogen mustard, eoposide, cis-platinum and WB4291.

The sLDL nanoparticles of the present invention could be used to transport anti-tumor agents into brain tumors and other tumors of the central nervous system when coupled with local delivery techniques such convection-enhanced delivery (CED) and other methods known to those of skill in the art.

The synthetic LDL nanoparticles of the present invention can further be used as valuable in vivo imaging tools, not only for brain cancers and other brain diseases, but also for any tumors possessing LDLRs and thus greatly aid in diagnosing cancers of the nervous system.

II. Definitions

The term "LDL" or "low density lipoprotein" refers to a class of naturally occurring lipoprotein particles, varying in their size (18-25 nm in diameter) and contents, which carry cholesterol in the blood and around the body, for use by cells. The LDL contains the apolipoproteins B-100 (Apo B-100, a protein with 4536 amino acid residues). It also contains antioxidative vitamins (vitamin E or carotinoids). It is commonly referred to as "bad cholesterol" due to the link between high LDL levels and cardiovascular disease.

The term "LDL receptor" or "LDLR" refers to a receptor that is expressed and presented on the surface of cells, and is responsible for binding LDL particles. The LDLR ligand is the ApoB100 glycoprotein on the surface of the LDL particle.

The term "LDLR binding domain" refers to any protein domain or amino acid sequence that can specifically bind the LDLR. For instance, the nine amino acid domain corresponding to residues 3359-3367 of ApoB100 is an example of an LDLR binding domain. It is well known to those of skill in the art that other amino acid sequences with conservative substitutions of residues 3359 to 3367 of ApoB100 can be generated to bind the LDLR and thus can be considered an LDLR binding domain.

The term "lipid moiety" refers to the lipid portion of the sLDL nanoparticle. The lipid portion can be made according to methods described herein, or any suitable method of forming a liposome-type particle as known to those of skill in the art.

The term "synthetic LDL nanoparticles" or "sLDL nanoparticle" refers to a low density lipoprotein particle comprising a lipid portion and synthetic chimeric peptides. The lipid portion and the chimeric peptides can be admixed, covalently linked, or non-covalently linked. The synthetic chimeric peptides of the sLDL nanoparticle comprise an amphipathic α-helix and a lipid receptor binding domain. The amphipathic α-helices confer lipid affinity to the synthetic peptides, while LDL receptor binding domain confers affinity for LDL receptors found on the surface of cells. The lipid portion of the sLDL nanoparticle is a lipid microemulsion consisting of 3:2:1 molar ratio of phospholipids (PL), triglyceride (TG) and cholesteryl ester (CE) or any other molar ratio of lipid components that allows for microemulsification and ultimately produces a particle of 10-30 nm in size. Alternatively, the lipid microemulsion can consist of PL and TG. In some embodiments, the PL and TG are in a molar ratio of 3:2. In other embodiments, the lipid microemulsion can consist of any lipids known in the art.

It is well known to those of skill in the art that small lipid particles or liposomes can be generated by a variety of methods as described in, e.g., Szoka et al., Ann. Rev. Biophys. Bioeng. 9:467 (1980); U.S. Pat. Nos. 4,186,183, 4,217,344, 4,235,871, 4,261,975, 4,485,054, 4,501,728, 4,774,085, 4,837,028, 4,946,787; PCT Publication No. WO 91/17424; Szoka & Papahadjopoulos, Proc. Natl. Acad. Sci. USA 75: 4194-4198 (1978); Deamer & Bangham, Biochim. Biophys. Acta 443: 629-634 (1976); Fraley et al., Proc. Natl. Acad. Sci. USA 76: 3348-3352 (1979); Hope et al., Biochim. Biophys. Acta 812: 55-65 (1985); Malyer et al., Biochim. Biophys. Acta 858: 161-168 (1986); Williams et al., Proc. Natl. Acad. Sci. USA 85: 242-246 (1988), Liposomes, ch. 1 (Ostro, ed., 1983); and Hope et al., Chem. Phys. Lip. 40: 89 (1986). Suitable methods include, e.g., sonication, extrusion, high/pressure/homogenization, microfluidization, detergent dialysis, calcium-induced fusion of small liposome vesicles, and ether-infusion methods, all well known in the art. One method produces multilamellar vesicles of heterogeneous sizes. In this method, the vesicle-forming lipids are dissolved in a suitable organic solvent or solvent system and dried under vacuum or an inert gas to form a thin lipid film. If desired, the film may be re-dissolved in a suitable solvent, such as tertiary butanol, and then lyophilized to form a more homogeneous lipid mixture which is in a more easily hydrated powder-like form. This film is covered with an aqueous buffered solution and allowed to hydrate, typically over a 15-60 minute period with agitation. The size distribution of the resulting multilamellar vesicles can be shifted toward smaller sizes by hydrating the lipids under more vigorous agitation conditions or by adding solubilizing detergents such as deoxycholate. For instance, suspending the lipids of choice in solution and sonicating the solution can be used to generate lipid microemulsions containing lipid particles. The resulting particles of choice can then be separated using various density gradients or using size exclusion chromatography. Other methods are well known to those of skill in the art.

Following liposome preparation, the liposomes that have not been sized during formation may be sized by extrusion to achieve a desired size range and relatively narrow distribution of liposome sizes. A size range of about 0.2-0.4 microns allows the liposome suspension to be sterilized by filtration through a conventional filter, typically a 0.22 micron filter. The filter sterilization method can be carried out on a high through-put basis if the liposomes have been sized down. Several techniques are available for sizing liposomes to a desired size. One sizing method is described in U.S. Pat. Nos. 4,529,561 or 4,737,323. Sonicating a liposome suspension either by bath or probe sonication produces a progressive size reduction down to small unilamellar vesicles less than about 0.05 microns in size. Homogenization is another method which relies on shearing energy to fragment large liposomes into smaller ones. In a typical homogenization procedure, multilamellar vesicles are recirculated through a standard emulsion homogenizer until selected liposome sizes, typically between about 0.1 and 0.5 microns, are observed. The size of the liposomal vesicles may be determined by quasi-electric light scattering (QELS) as described in Bloomfield, Ann. Rev. Biophys. Bioeng., 10: 421-450 (1981). Average liposome diameter may be reduced by sonication of formed liposomes. Intermittent sonication cycles may be alternated with QELS assessment to guide efficient liposome synthesis.

The term "amphipathic alpha helix" or "amphipathic α-helix" refers to a peptide helix with a polar face that comprises primarily hydrophilic amino acids (e.g., Asp, Glu, Gly, Ser, Thr, Cys, and Tyr) and nonpolar face that comprises primarily hydrophobic amino acids (e.g., Leu, Ala, Val, Ile, Pro, Phe, Trp and Met) (see, e.g., Kaiser and Kezdy, Ann. Rev. Biophys. Biophys. Chem. 16: 561 (1987) and Science 223:249 (1984). The polar face of an amphipathic α-helix typically comprises an "alignment of negatively charged amino acids" or "an alignment of acidic amino acids," i.e., a series of negatively charged or acidic amino acids (e.g., amino acids that are acidic at substantially neutral pH such as Asp or Glu or amino acids that have been modified so that they are acidic at approximately neutral pH such as modified Gly, Ser, Thr, Cys, or Tyr) positioned approximately evenly (e.g. at about every two to three helical turns) within the peptide sequence. Thus, the amino acid sequence of an amphipathic α-helix typically alternates between hydrophilic and hydrophobic residues every 3 to 4 residues, since the α-helix makes a turn approximately every 3.6 residues. Amphipathic α helices play a role in both intra- and intermolecular protein-protein interactions, and proteins and lipoproteins (e.g., including apolipoproteins) comprising amphipathic α-helices have been postulated to play a role in lipid (e.g., HDL) function (see, e.g. Anantharamaiah et al., Adv Exp Med Biol. 285:131-40 (1991)). The structure and function of amphipathic α-helices has been reviewed in, e.g., Segrest et al., Proteins 8(2): 103-17 (1990). In silico methods of identifying amphipathic α helices have been described by. e.g., Jones et al., J Lipid Res. 33(2):141-66 (1992). Multiple proteins comprising amphipathic α-helices have been identified including, e.g., apolipoproteins and serum amyloid proteins.

The term "apolipoprotein" or "Apo" or "exchangeable apolipoprotein" refers to any one of several helical proteins that can combine with a lipid (i.e., solubilize the lipid) to form a lipoprotein and are a constituent of chylomicrons, HDL, and VLDL. Apolipoproteins exert their physiological effect on lipid metabolism by binding to and activating specific enzymes or transporting proteins or lipids to cells via specific receptors: e.g. LDLR or LRP.

"ApoB100" or "apolipoprotein B100" refers to the 514 glycoprotein on the surface of the naturally occurring LDL. This lipid binding protein is very large and consists of a hydrophobic domain, amphipathic beta sheets and amphipathic α-helices. A protein sequence of the human apoB100 is identified by GenBank accession number NP_000375; which is the protein product of the nucleic acid sequence identified by GenBank accession number M15421.

"Therapeutic treatment" and "cancer therapies" and "cancer therapy reagents" refers to apoptosis-mediated and non-apoptosis mediated cancer therapies that treat, prevent, or inhibit cancers, including chemotherapy, hormonal therapy (e.g., androgens, estrogens, antiestrogens (tamoxifen), progestins, thyroid hormones and adrenal cortical compounds), radiotherapy, and immunotherapy (e.g., ZEVALIN, BEXXAR, RITUXAN (rituximab), HERCEPTIN).

"Cancer" or "carcinoma" refers to a number of human illnesses including sarcomas, adenocarcinomas, lymphomas, leukemias, etc., including solid and lymphoid cancers, kidney, breast, lung, bladder, colon, ovarian, prostate, pancreas, stomach, brain, head and neck, skin, uterine, testicular, glioma, esophagus, and liver cancer, including hepatocarcinoma, lymphoma, including B-acute lymphoblastic lymphoma, non-Hodgkin's lymphomas (e.g., Burkitt's, Small Cell, and Large Cell lymphomas) and Hodgkin's lymphoma, leukemia (including AML, ALL, and CML), multiple myeloma, mantle cell lymphoma, Waldenstrom's macrogobulinemia, and Philadelphia positive cancers.

"Chemotherapeutic drugs" include conventional chemotherapeutic reagents such as alkylating agents, anti-metabolites, plant alkaloids, antibiotics, and miscellaneous compounds e.g., cis-platinum, CDDP, methotrexate, vincristine, adriamycin, bleomycin, and hydroxyurea. The drugs can be administered alone or combination ("combination chemotherapy").

A "small organic molecule" refers to an organic molecule, either naturally occurring or synthetic, that has a molecular weight of more than about 50 daltons and less than about 2500 daltons, preferably less than about 2000 daltons, preferably between about 100 to about 1000 daltons, more preferably between about 200 to about 500 daltons.

An "siRNA" molecule or an "RNAi molecule" refers to a nucleic acid that forms a double stranded RNA, which double stranded RNA has the ability to reduce or inhibit expression of a gene or target gene when the siRNA expressed in the same cell as the gene or target gene. "siRNA" thus refers to the double stranded RNA formed by the complementary strands. The complementary portions of the siRNA that hybridize to form the double stranded molecule typically have substantial or complete identity. In one embodiment, an siRNA refers to a nucleic acid that has substantial or complete identity to a target gene and forms a double stranded siRNA. The sequence of the siRNA can correspond to the full length target gene, or a subsequence thereof. Typically, the siRNA is at least about 15-50 nucleotides in length (e.g., each complementary sequence of the double stranded siRNA is 15-50 nucleotides in length, and the double stranded siRNA is about 15-50 base pairs in length, preferably about 20-30 base nucleotides, preferably about 20-25 or about 24-29 nucleotides in length, e.g., 20, 21, 22, 23, 24, 25, 26, 27, 28, 29, or 30 nucleotides in length.

By "therapeutically effective amount or dose" or "sufficient amount or dose" herein is meant a dose that produces effects for which it is administered. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy,* 20th Edition, 2003, Gennaro, Ed., Lippincott, Williams & Wilkins.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer. Amino acid polymers may comprise entirely L-amino acids, entirely D-amino acids, or a mixture of L and D amino acids.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The terms "nucleic acid" and "polynucleotide" are used interchangeably herein to refer to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); Rossolini et al., Mol. Cell. Probes 8:91-98 (1994)). The term nucleic acid is used interchangeably with gene, cDNA, mRNA, oligonucleotide, and polynucleotide.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologues, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, Proteins (1984)).

Macromolecular structures such as polypeptide structures can be described in terms of various levels of organization. For a general discussion of this organization, see, e.g., Alberts et al., Molecular Biology of the Cell (3rd ed., 1994) and Cantor and Schimmel, Biophysical Chemistry Part I: The Conformation of Biological Macromolecules (1980). "Primary structure" refers to the amino acid sequence of a particular peptide. "Secondary structure" refers to locally ordered, three dimensional structures within a polypeptide. These structures are commonly known as domains. Domains are portions of a polypeptide that form a compact unit of the polypeptide and are typically 50 to 350 amino acids long. Typical domains are made up of sections of lesser organization such as stretches of β-sheet and α-helices or random coils. "Tertiary structure" refers to the complete three dimensional structure of a polypeptide monomer. "Quaternary structure" refers to the three dimensional structure formed by the noncovalent association of independent tertiary units. Anisotropic terms are also known as energy terms.

A "label" or "detectable label" is a composition detectable by spectroscopic, photochemical, biochemical, immunochemical, or chemical means. For example, useful labels include radioisotopes (e.g., $^3H$, $^{35}S$, $^{32}P$, $^{51}Cr$, or $^{125}I$), fluorescent dyes, electron-dense reagents, enzymes (e.g., alkaline phosphatase, horseradish peroxidase, or others commonly used in an ELISA), biotin, digoxigenin, or haptens and proteins for which antisera or monoclonal antibodies are available (e.g., the polypeptide encoded by SEQ ID NOS: 6, or 7 can be made detectable, e.g., by incorporating a radiolabel into the peptide, and used to detect antibodies specifically reactive with the peptide).

The terms "identical" or percent "identity," in the context of two or more nucleic acids or polypeptide sequences, refer to two or more sequences or subsequences that are the same or have a specified percentage of amino acid residues or nucleotides that are the same (i.e., 60% identity, preferably 65%, 70%, 75%, 80%, 85%, 90%, or 95% identity over a specified region such as Helix 1, 6, 7, 9, or 10 of Apo A-I), when compared and aligned for maximum correspondence over a comparison window, or designated region as measured using one of the following sequence comparison algorithms or by manual alignment and visual inspection. Such sequences are then said to be "substantially identical." This definition also refers to the compliment of a test sequence. Preferably, the identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of nucleic acids and proteins to the chimeric protein of the present invention or portions thereof, the BLAST and BLAST 2.0 algorithms and the default parameters discussed below are used.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

A preferred example of algorithm that is suitable for determining percent sequence identity and sequence similarity are the BLAST and BLAST 2.0 algorithms, which are described in Altschul et al., Nuc. Acids Res. 25:3389-3402 (1977) and Altschul et al., J. Mol. Biol. 215:403-410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information (www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments;

or the end of either sequence is reached. The BLAST algorithm parameters W, T, and X determine the sensitivity and speed of the alignment. The BLASTN program (for nucleotide sequences) uses as defaults a word length (W) of 11, an expectation (E) of 10, M=5, N=−4 and a comparison of both strands. For amino acid sequences, the BLASTP program uses as defaults a word length of 3, and expectation (E) of 10, and the BLOSUM62 scoring matrix (see Henikoff & Henikoff, Proc. Natl. Acad. Sci. USA 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, Proc. Nat'l. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

A further indication that two nucleic acid sequences or proteins are substantially identical is that the protein encoded by the first nucleic acid is immunologically cross reactive with the protein encoded by the second nucleic acid, as described below. Thus, a protein is typically substantially identical to a second protein, for example, where the two peptides differ only by conservative substitutions. Another indication that two nucleic acid sequences are substantially identical is that the two molecules hybridize to each other under stringent conditions, as described below.

III. Synthetic LDL Nanoparticles (sLDL)

In one embodiment, the invention provides for synthetic LDL nanoparticles comprising a lipid composition and synthetic chimeric peptides. The synthetic chimeric peptides of the sLDL nanoparticle comprise an amphipathic α-helix and a lipid receptor binding domain. The amphipathic α-helices confer lipid affinity to the synthetic peptides, while LDL receptor binding domain confers affinity for LDL receptors found on the surface of cells. The peptides can be chemically synthesized, translated in vitro, or recombinantly produced using methods know to those of skill in the art. The nanoparticle comprises the lipid moiety and the chimeric peptide, which are admixed, covalently linked or noncovalently linked. The nanoparticle is produced as described herein or can be made by methods known to those of skill in the art.

In one embodiment, the mean LDL nanoparticle size is 20 nm, but can be 10 nm-30 nm. In some embodiments, the sLDL nanoparticle is between 10-20 nm in size. The synthetic peptides can be complexed with microemulsions of 3:2:1 molar ratio of phospholipids (PL), triglyceride (TG) and cholesteryl ester (CE). In some embodiments, the phospholipid is egg yolk phosphatidylcholine. Suitable triglycerides that can be used include but are not limited to, triolein (TO) and tripalmitate. Suitable cholesteryl esters that can be used include but are not limited to, cholesteryl oleate (CO) or cholesteryl palmitate (CP). In another embodiment, the composition of the core lipids, CE and TG are altered in order to alter the size of the emulsion. In another embodiment, the ratio of lipids is 3:2:1 molar ratio of PL:TG:CE. Other molar ratios that can be used include PL:CE:TG of 3:2:1 and PL:CE:TG of 3:2:0.5. In some embodiments, the cholesteryl ester is omitted from the microemulsion. In some embodiments the synthetic peptides can be complexed with microemulsions of PL and TG in the ratio of 3:2

The microemulsions can be made by extrusion of the lipids through a 30 nm filter. For example, the lipids are sonicated at 4° C. in the presence of 20 μM BHT and $N_2$ for sufficient time (e.g., about 1 hour), then extruded through a series of filters to obtain lipid particles having a suitable size. In one embodiment, the microemulsion is extruded through a 0.1 μm (100 nm) filter, then a 0.03 μm (30 nm) filter and isolated. After isolation, the lipid microemulsion is introduced to a synthetic chimeric peptide, whereby the peptides bind onto the surface of the nanoparticles. In another embodiment, the size of the isolated peptide-stabilized lipid particles is confirmed by column chromatography techniques, such as Fast Protein Lipid Chromatography (FPLC).

In one embodiment the synthetic chimeric peptides comprise an amphipathic α-helix and a LDL receptor binding domain. In another embodiment, the synthetic chimeric peptide comprises two amphipathic α-helices, one on each side of the LDL receptor binding domain.

The LDL receptor binding domain can be any LDL receptor binding domain known. In one embodiment, the LDL receptor binding domain is the 9 amino acids of ApoB100 that comprise the minimal LDLR binding domain, RLTRKRGLK (SEQ ID NO: 1). It is well known in the protein art that conservative mutations may still allow binding. For example, replacing the second lysine with isoleucine may still confer binding to the LDLR. As another example, replacing the seventh amino acid, glycine, with alanine might still confer binding. These two examples are meant to just illustrate some of the possible substitutions, and are, by no means, meant to be limiting. A person of skill in the art know very well which conservative substitutions can be made across all 9 of the amino acids of SEQ ID NO: 1 that would still allow binding of the LDLR-binding domain to LDLR.

In another embodiment where non-brain tumors are targeted, the LDL receptor related protein (LRP) binding domain of ApoE can be used for targeting the LRP receptor as well as the apoB receptor.

In one embodiment, the amphipathic α-helix chosen for the LDL nanoparticles binds to the lipid surface of the synthetic lipid nanoparticle and thus stabilizes the particle while the LDL receptor binding domain remains free to interact with the LDL receptor. The use of peptides would likely form small particles containing several peptides (see FIG. 3B). An advantage of using the LDLR binding domain of the apolipoprotein instead of using full length apolipoproteins, such as apoB100, is due to the difficulty of working with full length apolipoproteins due to their large size. The availability of several peptides on the surface of the synthetic LDL should increase binding efficiency. It is also contemplated that several types of chimeric peptides (i.e., chimeric peptides having different sequences) can be used to stabilize the same synthetic LDL nanoparticle.

The peptides may be made and purified by methods known in the art, preferably by in vitro automated synthesis, but also by recombinant DNA methods or in vitro translation. Furthermore, these peptides can be synthesized using L-amino acids, non-natural or other modified amino acids, as is known in the art, in order to synthesize peptides which can act upon targets in the body and be degraded, yet do not interfere with normal protein function. The peptides can be stored in lyophilized form and dissolved in aqueous buffers or water prior to use. For the purposes of experimental use, the peptides are dissolved in sterilized degassed buffers to optimize biological activity which remains stable over 1-3 months at 4° C.

The amphipathic α-helix can be 10 to 22 amino acids (a.a.) in length, more preferably, 18 to 22 a.a. in length. Any amphipathic α-helix, derived from a known apolipoprotein or a synthetic amphipathic α-helix peptide can be used if the amphipathic α-helix peptide binds well to lipids, which can be determined empirically. Apolipoproteins whose amphipathic α-helices can be used for the chimeric peptides, include human native ApoA-I amino acid sequence (GenBank Accession Number: P02647 locus APA1_HUMAN), ApoA-IV (GenBank Accession Number P06727), ApoE (GenBank Accession Number P02649), ApoC-I (GenBank Accession Number NP_001636), and ApoC-II (GenBank Accession Number NP_000474), the Accession sequences which are hereby incorporated by reference. In a preferred embodiment, the amphipathic α-helix is the 18A Segrest peptide (SEQ ID NO: 2) or an amphipathic α-helix from Apolipoprotein AI (GenBank Accession No: CAA01253) such as ApoAI helix 9, the Accession sequence hereby incorporated by reference.

In one embodiment, the chimeric synthetic peptide comprises the LDL receptor binding domain of apoB100 flanked at its amino terminal region by 18 amino acids that form an amphipathic α-helix, such as the 18A peptide originally described by Segrest et al (Vitols, S. et al, *Blood* 63:1186-1193 (1984)). The Segrest peptide was originally designed to bind to cell membranes and was found to also avidly bind phospholipids. In some embodiments, the synthetic chimeric peptide can be capped at the N-terminus, the C-terminus or both at the N and C termini.

In one embodiment, the peptide is made up of 29 amino acids, the sequence comprising the 18 amino acid amphipathic helix and residues 3359-3369 of the apolipoprotein, apoB100, having a sequence:

```
DWLKAFYDKVAEKLKEAFRLTRKRGLKLA.    (SEQ ID NO: 3)
```

The underlined region is the LDL receptor binding domain (LDLR). In some embodiments, the peptide used does not comprise the upstream and downstream flanking regions of the LDL receptor binding domain and native protein, such as the 22 amino acid peptide described in Baille et al (Baillie, G. et al., *J Lipid Res* 43:69-73 (2002)). In some embodiments, the chimeric peptide has the sequence of SEQ ID NO: 3, SEQ ID NO: 4, SEQ ID NO: 5, SEQ ID NO: 6, SEQ ID NO: 7 or SEQ ID NO: 8, or a sequence having at least 70%, 80%, 85%, 90%, 95%, 98%, 99%, or 100% homology to the recited sequences.

The variants of the sequences described herein may have sequences where native residues are conservatively substituted for one another. For example, negatively charged residues E or D can be conservatively substituted for the other at residues 1, 8, 12 or 16 of the Segrest peptide. The term "conservative substitution" means a substitution where an amino acid residue is substituted for another in the same class, where the amino acids are divided into non-polar, acidic, basic and neutral classes, as follows: non-polar:(A), Val (V), Leu (L), Ile (I), Phe (F), Trp (W), Pro (P), Met (M); acidic: Asp (D), Glu (E); basic: Lys (K), Arg (R), His (H); uncharged polar: Gly (G), Ser (S), Thr (T), Cys (C), Asn (N), Gln (Q), Tyr (Y). A non-conservative amino acid substitution is one where the residues do not fall into the same class, for example, substitution of a basic amino acid for a neutral or non-polar amino acid.

In another embodiment, to increase binding of the peptide to the surface of lipid emulsions, an amphipathic helix with greater hydrophobicity linked to the LDL receptor domain is used. For example, the 18A Segrest peptide can be modified to contain four phenylalanines (an increase of 2 F amino acid, substitutions of F3 and F14) to increase hydrophobicity. The resulting chimeric peptide would have the sequence,

```
DWFKAFYDKVAEKFKEAFRLTRKRGLKLA.    (SEQ ID NO: 4)
```

The chimeric peptides of the present invention include those that are greater than 90% homologous to the recited exemplary sequences. By the term "homology" or "homologous," it is meant an amino acid similarity measured by the program, BLAST (Altschul et al (1997), "Gapped BLAST and PSI-BLAST: a new generation of protein database search programs", Nucleic Acids Res. 25:3389-3402), as found at http://www.ncbi.nlm.nih.gov/blast/Blast.cgi and expressed as—(% identity n/n). In measuring homology between a peptide and a protein of greater size, homology is measured only in the corresponding region; that is, the protein is regarded as only having the same general length as the peptide, allowing for gaps and insertions.

The amphipathic α-helical sequences derived from certain helices found within a native apolipoprotein may not consistently match the numbering in GenBank because the peptides are often synthesized with a leader amino acid or peptide (referred to as precursor) that is not present in the mature plasma form of the protein. However, it should be rudimentary for one with skill in the art to match the sequences and find the precursor.

In addition to the above substitutions, various conservative substitutions may be made in non-critical regions of the present peptides likely without affecting activity if the polar interface of the amphipathic helix is not interrupted. Conservative substitutions of such residues as A, L, I, M, and V, may not be critical. Caution may be required in making substitutions involving residues such as tryptophan and phenylalanine on the hydrophobic face of the helix because these large hydrophobic residues increase the hydrophobicity of the helices and likely impart good lipid binding affinity. In some helices, the proline residues also may be critical as linkers to the helices, therefore caution should likely be used in making any substitutions of prolines.

In embodiments in which the synthetic chimeric peptide comprises two amphipathic α-helices, one on each side of the LDL receptor binding domain, it is contemplated that the same amphipathic α-helix, adjacent or non-adjacent amphipathic α-helices from the same apolipoprotein, or amphipathic α-helices from different apolipoproteins are used on either side of the LDL receptor binding domain. For example, in one embodiment, helix 9 and helix 10 from ApoA-I are used on either side of the LDL receptor binding domain.

In one embodiment, the peptide is capped in the amino-terminus (N-terminus) with an acetyl group and at the carboxy-terminus (C-terminus) with an amide group to stabilize the peptide.

Figure 3:
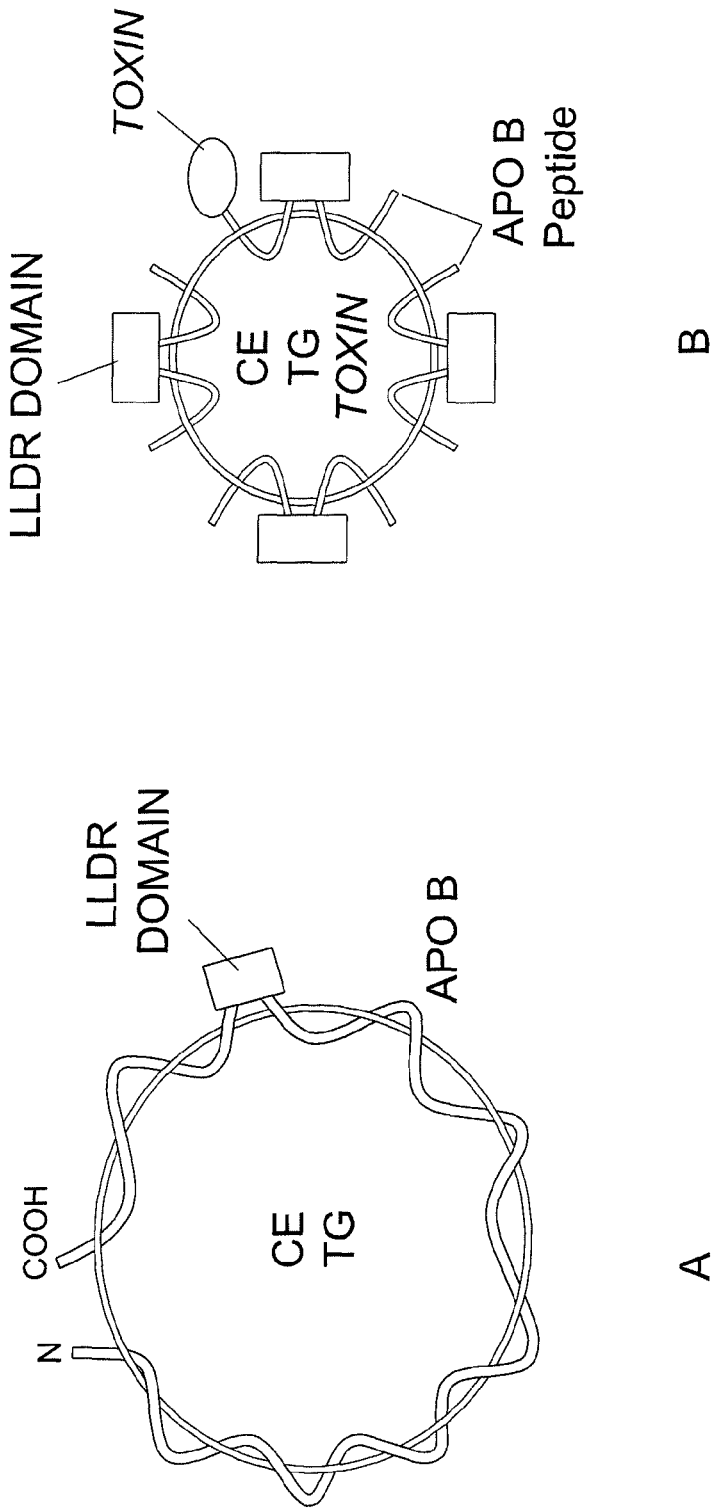
FIG. 3. A depicts a cartoon of the native LDL nanoparticle. Only one large protein, apoB100, is on the surface of the molecule, and the molecule is much larger than the synthetic LDL (shown in FIG. 3. B).

As illustrated in FIG. 3B, synthetic LDL nanoparticles can comprise one or more chimeric peptides and a therapeutic moiety, which can be admixed with the particle, or covalently or non-covalently linked to the lipid moiety or to a portion of the chimeric peptide. Lipophilic cell toxins can be taken up by the lipid core of the particle. Hydrophilic drugs, e.g., doxorubicin, can be attached covalently or non-covalently to the amphipathic alpha helix moiety of the peptide. The hydrophobic core of the sLDL consisting of the fatty acid moiety of phospholipids, triglycerides and cholesteryl esters, can be used for the incorporation of hydrophobic, lipophilic drugs such as camptothecin, irinotecan, SN-38, and lipophilic paclitaxel derivative.

In another embodiment, where the drug or toxin is not attached to the amphipathic α-helix, it is contemplated that the drugs are loaded into the LDL nanoparticles. For drugs that are hard to solubilize, it is contemplated that techniques may be used, such as lowering the pH or using DMSO to solubilize the drug for loading. Examples of such drugs include but are not limited to doxirubicin, camptothecin, irinotecan, SN-38, paclitaxel, paclitaxel oleate, nitrogen mustard, etoposide, and WB4291.

Therapeutic moieties include, but are not limited to small molecules, therapeutic peptides and proteins, antibodies, radioisotopes, siRNA and nucleic acids for gene therapy, toxins such as anthrax toxin, shiga toxin, A chain of diphtheria toxin, *Pseudomonas* exotoxin A, and known anti-cancer agents such as taxol, paclitaxel oleate, paclitaxel, doxirubicin (adriamycin, analogs, and derivatives)

To test whether the synthetic LDL nanoparticles are functional, an indirect assay system can be used, consisting of U937 cells that require exogenous cholesterol for growth such as the assay described in Example 3. The assay system can test whether the peptides developed have the ability to induce reasonable growth of the cells while growth is inhibited by co-incubating with an anti-LDLR antibody. In another embodiment, cell studies using human SF-767 and U-251 glioblastoma cell lines are conducted to determine whether the sLDL binds to the cell surface LDL receptor and is internalized. In another embodiment, using SF-767 and other GBM cell lines, both binding affinity and uptake can be quantified and tested for the ability of these ligands to bind to and be internalized by GBM cells.

IV. Drug Delivery to the Tumor

Delivery of large molecules such as monoclonal antibodies and LDL to the brain is severely limited by the blood brain barrier (BBB). To circumvent this problem, it is possible to use local drug delivery to the brain tumor. This approach provides (1) an effective means of bypassing the BBB, (2) minimal systemic toxicity and (3) high concentrations of the drug in the tumor. Early intratumoral studies used simple diffusion but this technique has an inherent problem in that diffusion is dependent on a concentration gradient and the size of the therapeutic agent. By simple diffusion large molecules such as LDL (~25 nm) would have very limited diffusion and would be restricted to a few mm from the source (Haroun, R. I. et al., *Curr Opin Oncol* 12:187-193 (2000)). To circumvent the problem of systemic drug delivery to the brain, a method for local intratumoral delivery has been developed; this technology is termed convection-enhanced delivery (CED) (Bobo, R. H. et al., *Proc Natl Acad Sci USA* 91:2076-2080 (1994); Morrison, P. F. et al., *Am J Physiol* 266:R292-305 (1994)); it holds promise as a strategy for delivering LDL-based therapeutics directly into brain tumors.

Local delivery of large molecules is improved by convection-enhanced delivery (Bobo, R. H. et al., *Proc Natl Acad Sci USA* 91:2076-2080 (1994); Morrison, P. F. et al., *Am J Physiol* 266:R292-305 (1994)). This technique uses a pressure gradient established at the tip of the infusion catheter to distribute the drug in the interstitial space. Unlike simple diffusion, CED allows the uniform distribution of therapeutic agents up to 3 cm from the point of infusion (Laske, D. W. et al., *J Neurosurg* 87:586-594 (1997); Laske, D. W. et al., *Nat Med* 3:1362-1368 (1997); Yang, W. et al., *Cancer Res* 57:4333-4339 (1997); Yang W. et al., *Cancer Res* 62:6552-6558 (2002)). It is to be expected that even under CED conditions that diffusion is dependent on the size of the molecule being injected. Thus the smaller the diameter of the particle, the more accessible it will be to the entire tumor mass. In a recent report on boron neutron capture therapy, it was postulated that small apoprotein-mediated LDL nanoparticles (<20 nm diameter) can possibly be used as boron agent carriers (Cumberlin R. L. *Int J Radiat Oncol Biol Physl* 54:992-998 (2002)). The difficulty with this concept is that plasma LDL mean particle size is 25 nm, not <20 nm; hence native LDL are likely not ideal for CED delivery of boronated compounds or other therapeutics to brain tumor cells. The synthetic LDL nanoparticle of the present invention has the properties of LDL, i.e., recognizes the LDLR, but also is considerably smaller in size than native particles, i.e., a nanoparticle.

The synthetic LDL nanoparticles of the present invention have potential commercial value as a novel way to deliver cytotoxins to GBM tumors as well as other central nervous system tumors. It has the potential to be used with radionuclides as an imaging agent to detect tumors. Presently most chemotherapeutics are systemically delivered to GBM; this limits the dose targeted to brain tumor cells; additionally many agents do not cross the blood brain barrier. The present delivery system is designed to work in conjunction with intratumoral delivery which would directly deliver the therapeutic to the brain after insertion of a catheter(s).

The synthetic LDL nanoparticles of the invention are also contemplated as finding use in delivery of chemotherapeutics to tumors found elsewhere in the body.

V. EXAMPLES

Example 1

LDLR Present In Vitro in Cell Lines and In Vivo

LDLR in human glioblastoma cell lines: It has previously been shown that the human glioma cell line, SF-767, can internalize boronated protoporphyrin (BOPP), and by employing fluorescence microscopy, it has been shown that this intrinsically fluorescing compound is localized in the lysosome (Callahan, D. E. et al., *Int J Radiat Oncol Biol Phys* 45:761-771 (1999)). Since porphyrins are known to bind to LDL, it was hypothesized that LDL-associated BOPP was endocytosed through the LDLR pathway; localization of BOPP in the lysosomes is consistent with this premise. To further demonstrate LDLR-dependent uptake, BOPP was incubated with LDLR positive and negative fibroblasts. Unlike LDLR positive cells, little BOPP was apparent in the LDLR negative cells. Moreover, when lipoprotein depleted serum was used for the uptake studies, there was little uptake of BOPP into either SF-767 cells or fibroblasts. Taken together these studies strongly suggested that glioblastoma cells express LDLR and present it on their surface and that BOPP associates with the LDL and is endocytosed via the LDLR.

The above studies provided little information on the number and affinity of LDLRs on the SF-767 cells; more importantly, it was uncertain whether uptake was unique for this GBM line or whether expression of LDLR receptors may be a more global marker of these malignant cells. To address these questions studies were carried out to determine the affinity of LDL for the LDLR on SF-767 cells and to determine the number of receptors on the cells. In addition, six other glioblastoma cell lines were also examined to determine whether LDLR expression was a common feature of these cells and whether cells exhibited variation in receptor affinity and number. To address these questions, LDL binding kinetics were determined using $^{125}$I-labeled LDL (Maletinska, L. et al., Cancer Res 60:2300-2303 (2000)). As noted in Table 1 (Maletinska, L. et al., Cancer Res 60:2300-2303 (2000)), the SF-767 show high affinity saturable binding and have a high number of LDLRs per cell (288,000). It is apparent from the table, that there is variability in the expression of the LDLR, as well as in binding affinity, by the different GBM lines all of which are from stage IV GBM. Two cell lines (SF-763 and A-172) have exceedingly high receptor numbers (>900,000) while two other lines, U-343 MG and SF-539 have numbers similar to SF-767. The U-251 MG cell line has low receptor numbers (128,000) while U-87 MG expressed none. Solubilization of the U-87 cells followed by SDS-PAGE and immunoblotting for the LDLR indicated that this line did possess LDLR. Since the U-87 cells have a propensity to round up, it is likely that this morphological change may have altered receptor conformation and accessibility. The in vitro cell studies suggest that the LDLR is likely to be a marker for these malignant cells and an important target for LDLR-based therapy. To determine whether LDLR is overexpressed in brain tumors in vivo current studies are underway to evaluate the presence of LDLR in GBM biopsies using immunohistochemistry.

Human GBM tissue obtained during surgery also shows positively staining cells (FIG. 1B). A preliminary evaluation of 14 human GBM samples indicates that a high proportion (71%) of the tumors possess LDLR throughout the tumor mass. These results suggest that the LDLR is an important target for anti-tumor therapeutics based on a LDL delivery system.

Example 2

Novel Synthetic LDL Using Chimeric Peptides Consisting of the LDLR Binding Domain and Lipid-Binding Amphipathic A-Helices It was hypothesized that by using lipid-binding amphipathic A-helixes coupled to the apoB LDLR binding domain we can generate small synthetic LDL, i.e., LDL nanoparticles. Preliminary studies indicate that an 18 amino acid (a.a.) amphipathic α-helix coupled with the nine a.a. LDLR binding domain of apoB100 is able to form stable complexes with lipid emulsions consisting of phospholipid, triglyceride and cholesteryl ester.

To generate LDLR-specific synthetic lipoprotein particles, a chimeric peptide that encompassed both the LDLR binding domain and an N-terminal sequence containing an amphipathic α-helix was designed. The amphipathic helices avidly bind lipid and form stable protein-lipid particles possessing the apoB100 LDLR binding sequence. The amphipathic helices used were the synthetic 18 a.a. class A α-helix described by Segrest and associates (Segrest, J. P. et al., Adv Protein Chem 45:303-369 (1994)) and an 11-mer naturally occurring α-helix from apoA-I. The class A α-helix has apposing polar/

TABLE 1

[125]I-labeled LDL Binding to GBM Cells.

| Cell Line | Number of experiments | $K_d^a$ (μg/ml) | $K_d$ (nM) | $B_{max}$ (ng/mg cell protein) | Number of LDL receptors/cell |
|---|---|---|---|---|---|
| SF-767 | 4 | 3.50 ± 1.05 | 6.98 ± 2.12 | 793 ± 105 | 288,000 ± 41,900 |
| SF-763 | 1 | 60.0 | 120 | 900 | 950,000 |
| A-172 | 1 | 62.0 | 124 | 1400 | 923,000 |
| U-87 MG[b] | 2 | — | — | — | — |
| U-251 MG | 2 | 38.0[c] | 76[c] | 225[c] | 128,000[c] |
| U-343 MG | 1 | 40.0 | 80 | 510 | 311,000 |
| SF-539 | 1 | 50.0 | 100 | 310 | 252,000 |

[a]$K_d$, a dissociation constant equal to concentration of $^{125}$I-LDL corresponding to half of maximal binding $B_{max}$ value; $B_{max}$, related to maximum binding capacity.
[b]There was no evidence of binding in the range of 0-120 μg $^{125}$I-LDL/ml.
[c]Average value from 2 experiments.

Demonstration of LDLR in vivo: One approach was to demonstrate the expression of LDLRs in the human U-251 MG cell line implanted intracerebrally into athymic rats and to ascertain, if present, whether the receptors were confined solely to the tumor. A second approach was to evaluate LDLRs in human GBM tissues obtained at surgery and embedded in paraffin. Expression and localization of LDLR in fixed and paraffin embedded sections were evaluated following immunohistochemical staining of sections. A LDLR specific polyclonal antibody (gift from Dr. Janet Boyles) was used to localize the receptor; this antibody also recognizes the LDLR in rat and monkey tissue. As shown in FIG. 1.A, implanted U-251 MG tumor in rats had a high degree of positively staining cells shown as dark cells in the lower right quadrant of the figure. This figure also reveals that there is minimal staining of cells in adjacent normal rat brain tissue (the upper left quadrant of the photo).

nonpolar faces oriented along the long axis of the helix; it is defined by a unique clustering of positively charged residues at the polar/nonpolar interface and by negatively charged residues at the center of the polar face. This peptide which, here termed, 18-A is known to have high lipid affinity (Yancey P. G. et al., Biochemistry 34:7955-7965 (1995); Palgunachari, M. N. et al., Arterioscler Thromb Vasc Biol 16:328-338 (1996)). The 11-mer helix (termed 11-A peptide) from helix 9 of apoA-I was chosen because it is small but can bind lipid; it was used to test whether a small amphipathic helix can work as effectively as the longer 18-A peptide in forming lipid complexes. For comparison, a sequence described by Baille et al. was used (Baillie, G. et al., J Lipid Res 43:69-73 (2002)), the sequence consisting of the receptor binding domain flanked by short segments of native apoB100 but retinoic acid and cholesterol were not used to cap the peptide. This peptide is termed B-peptide. Three peptides which were 22 to 29 amino acids in length and were capped at the N-terminus with an acetyl group and at the C-terminus with a amine group to stabilize the peptide were examined. The peptides were synthesized by Biosynthesis Inc., Lewisville, Tex. The sequences of the three peptides are as follows; the LDLR binding domain in each sequence is underlined.

B-peptide: YKLEGTTRLTRKRGLKLATALS (SEQ ID NO: 5), this sequence corresponds to a.a 3352-3374 of apoB100 and is similar to one described by Baille et al. (Baillie, G. et al., *J Lipid Res* 43:69-73 (2002)) except that the N- and C-terminal caps are different. The peptide possesses both N- and C-terminal flanking regions of the native protein.

11-A chimeric peptide: PALEDLRQGLLP RLTRKRGLKL (SEQ ID NO: 6), this peptide is a chimera made up of an N-terminal sequence possessing a short amphipathic helix (11-mer) plus proline based on helix 9 of apolipoprotein A-I and the LDLR binding domain.

18-A chimeric peptide: DWLKAFYDKVAEKLKEAF RLTRKRGLKLA (SEQ ID NO: 3), this peptide is a chimera made up of the LDLR binding domain and an N-terminal sequence possessing an 18-mer synthetic amphipathic α helix originally described by Segrest et al. (Segrest, J. P. et al., *Adv Protein Chem* 45:303-369 (1994)). The 18-mer peptide is known to avidly bind phospholipids thus forming peptide-lipid complexes. The peptide forms a single amphipathic helix and is similar to the class A domains present in exchangeable apolipoproteins in that basic residues are located at the polar/nonpolar interface and acidic residues at the center of the polar face.

The ability of the peptides to bind phospholipids was tested first. Phospholipid binding was used as a rapid screen for a peptide's ability to bind to the surface of a synthetic LDL-like nanoparticle. To make phospholipid complexes with peptides, egg yolk phosphatidylcholine (PC) and the cholate dialysis method were used similarly to what was previously employed to make synthetic nascent HDL particles (Segrest, J. P. et al., *J. Lipid Res* 33:141-166 (1992)). The PC-cholate micelles were incubated with the peptide overnight and then extensively dialyzed (dialysis membrane cutoff, 10,000 MW) to remove cholate and unbound peptide. The percent bound peptide, i.e., peptide that remains associated with the lipid micelles, was determined for each peptide and was 8%, 15% and 33%, for B-peptide, 11-A chimera and 18-A chimera, respectively. The B-peptide had poor lipid binding ability while the 11-mer peptide has low lipid binding compared to the 18-A chimera. These data strongly suggest that a peptide similar to the 18-A may be ideal for generating synthetic LDL.

The 18-A chimera was utilized for making core-containing synthetic LDL. The procedure reported by Baille et al. (Baillie, G. et al., *J Lipid Res* 43:69-73 (2002)) was used with modifications. Microemulsions were formed using egg yolk phospholipid (PL), triolein (TO) and cholesteryl olein (CO) (mole ratio of 3:2:1) and 20 μM butylhydroxytoluene (BHT); the microemulsions were extruded through an Avanti miniextruder first using 100 nm polycarbonate filters followed by 30 nm polycarbonate filters. The lipid emulsions were incubated with 1.27 mg/ml 18-A chimera and lipid association determined after extensive dialysis against Tris-saline buffer to remove uncomplexed peptide. Approximately 85% of the added synthetic peptide remained associated with the lipid emulsions.

Figure 4:
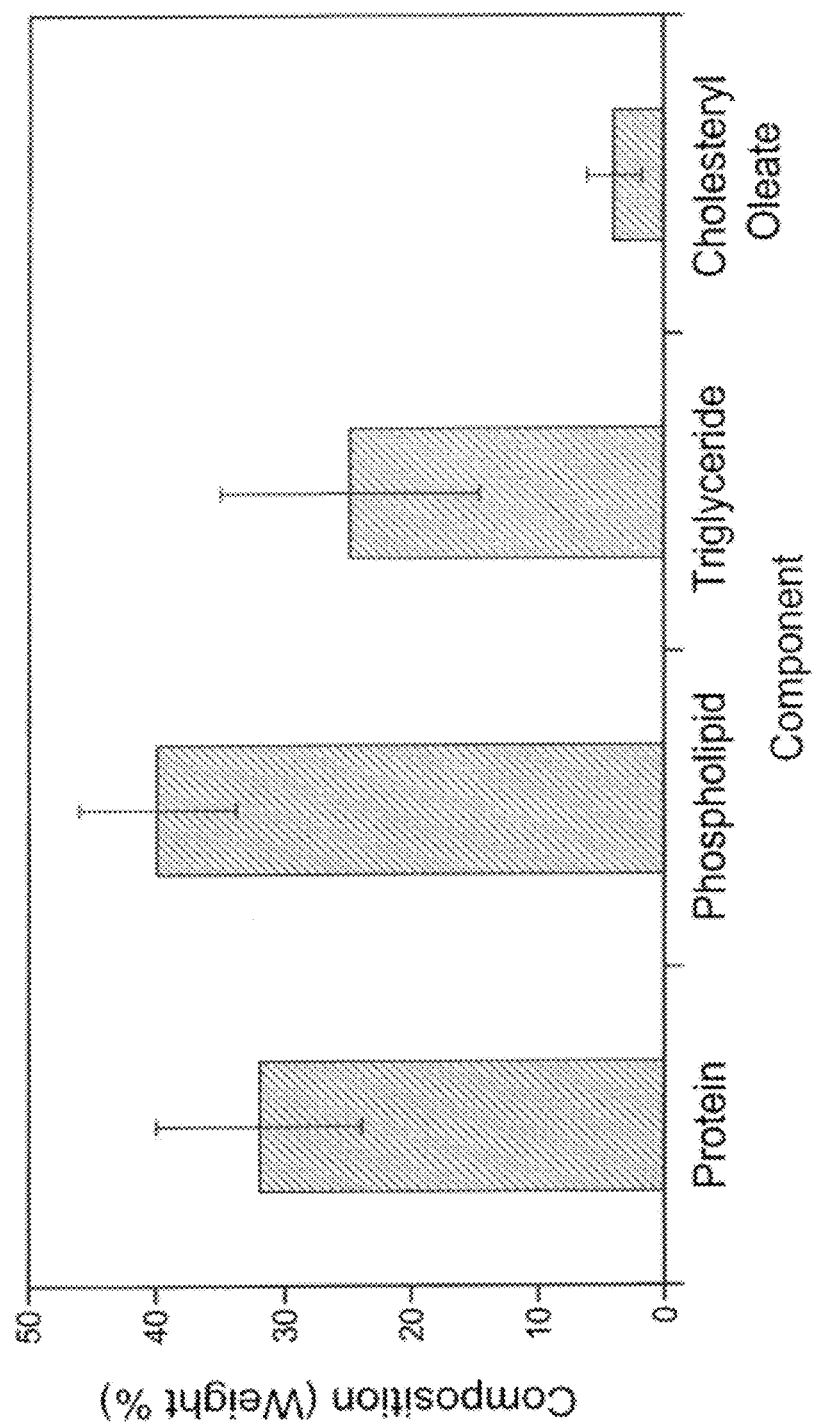
FIG. 4 depicts a graph of the composition of the synthetic LDL (sLDL) particle: 32% peptide, 68% lipid. The graph also shows that 82%±9% of peptide (n=11) remained bound to the sLDL nanoparticle after dialysis.

Characterization: Composition of particles was determined using the Markwell modification of the Lowry protein assay and enzymatic colorimetric assays for PL, TO and CO (Wako Kits). Size was determined by column chromatography using a Superose 6 fast protein liquid chromatography (FPLC) column. Samples were run at a flow rate of 0.5 mL/min and absorbance read at 280 nm. Referring now to FIG. 4, the composition of the synthetic LDL was characterized as 32% peptide, 68% lipid. 82%±9% of peptide (n=11) remained bound after dialysis. Native LDL: 25% protein, 75% lipid, and Native HDL: 50% protein, 50% lipid were characterized for comparison.

Studies were carried out to determine (1) whether the synthetic LDL represent a single population of particles and (2) whether the LDLR binding domain remains accessible after the peptide is associated with the lipid. To determine what types of synthetic LDL particles were generated, the lipidated 18-A chimera was subjected to sequential ultracentrifugation at density (d) 1.063 g/ml to isolate particles equivalent to, or less dense than, native LDL. Subsequently the solution was adjusted to d 1.21 g/ml to isolate particles in the d 1.063-1.21 g/ml range and those in the d>1.21 g/ml range. The latter particles are considered lipid-poor complexes while the d 1.063-1.21 particles are in the size and density range of high density lipoproteins (HDL). As seen in Table 2, almost 60% of the 18-A chimeric peptide is found associated with particles in the size and density range of HDL (HDL size is 7.5-15.0 nm). This was an unexpected finding but is very encouraging since smaller sized complexes will be better able to diffuse through the tumor mass than larger particles. The formation of small high density complexes is reproducible since it occurred with two separate batches of synthetic 18-A chimera complexes.

TABLE 2

Synthetic LDL: density distribution (percent) of 18-A chimera

| Density (g/ml) | Percent |
|---|---|
| d < 1.063 | 13 |
| d 1.063-1.21 | 58 |
| d > 1.21 | 29 |

Figure 2:
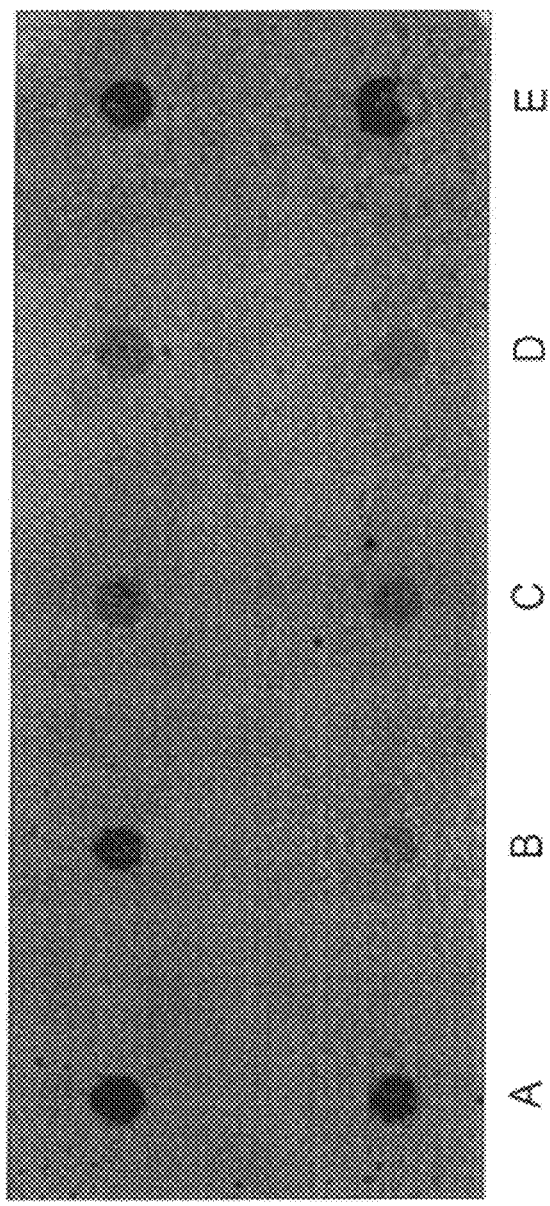
FIG. 2. depicts an immuno-dot blot of ultracentrifugal fractions of synthetic lipoprotein particles made with the apoB peptide. The MB47 antibody was used as the probe. Duplicate samples were loaded onto the dot blotter. Samples in the various lanes are as follows: A, d<1.063 g/ml; B, d 1.063-1.21 g/ml; C, d>1.21 g/ml; D, unfractionated synthetic particles and E, native plasma LDL. The immunoblot shows that the LDLR binding domain is accessible on the surface of the artificial particles as well as on native LDL.

To be a useful therapeutic macromolecule for targeting the LDLR, the apoB binding domain must remain accessible on the surface of the synthetic LDL. To evaluate this, immunoblots were carried out on the ultracentrifugal fractions using the MB47 monoclonal antibody (gift from Dr. Linda Curtiss) that is specific for the LDLR binding domain epitope. As seen in FIG. 2, all of the 18-A chimeric complexes react with the antibody indicating that the LDLR binding domain is exposed. Similar results were obtained using polyclonal antiserum to human apoB100.

Figure 5:
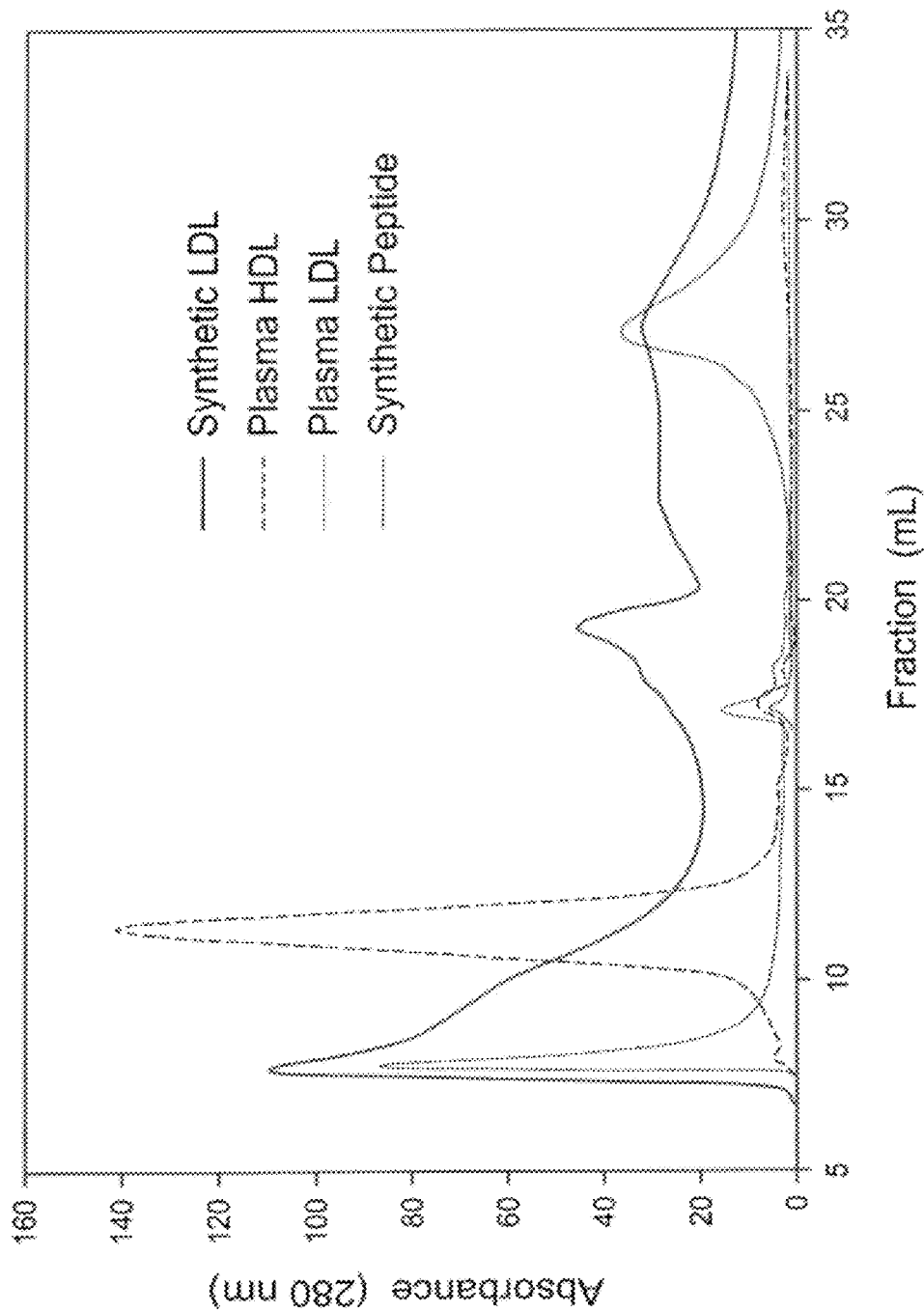
FIG. 5 depicts fast liquid chromatography (FPLC) scans showing the size of the major sLDL peak. As can be seen, the peak corresponding to the sLDL particle is intermediate between plasma LDL and HDL (used as reference particles). This size is consistent with the protein to lipid ratio which is intermediate to that of LDL and HDL.
Figure 6:
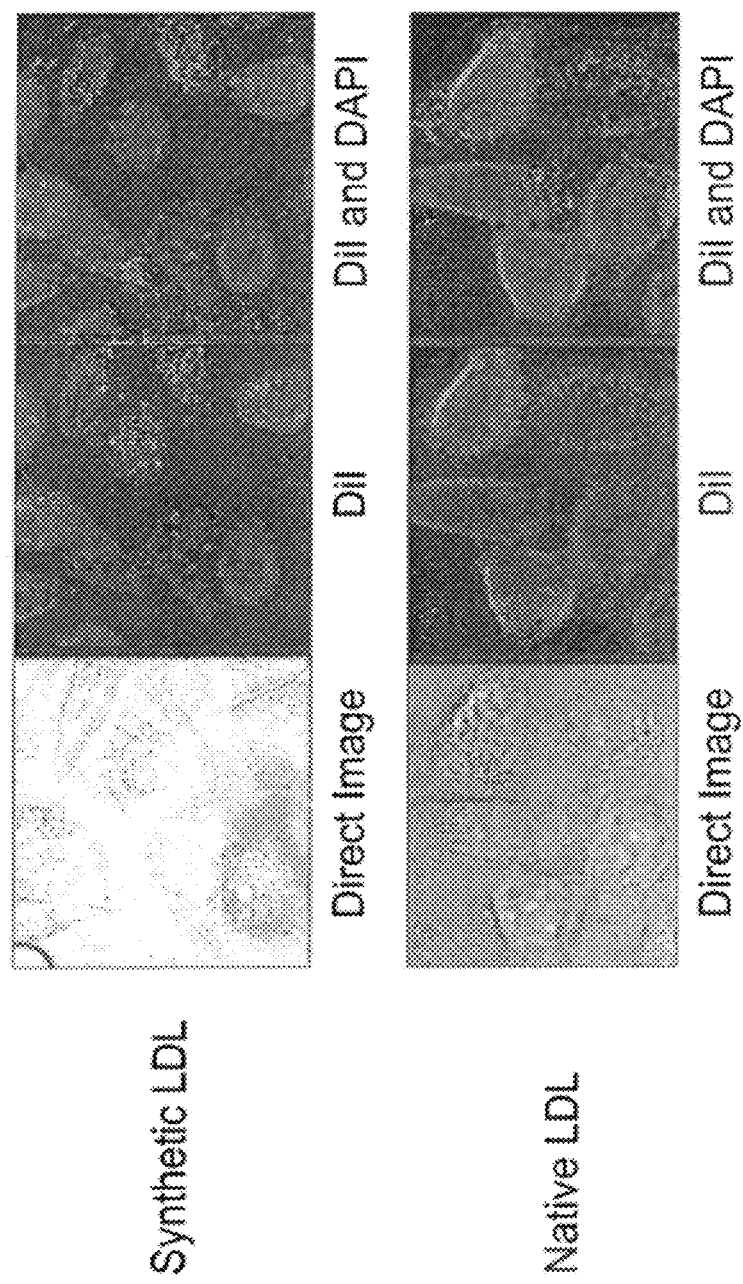
FIG. 6 depicts the distribution of fluorescently labeled sLDL (1.5 μM) and native LDL (10 μg/mL) on the surface of GBM SF-767 cells. Punctate distribution over the surface of the cell suggests that the sLDL, similar to native LDL, are bound to the LDL receptor on the cell surface. Cell binding was carried out at 4° C., 3 hr and the fluorescent lipid label, 3,3'-dioctadecylindocarbocyanine (DiI), was used to identify sLDL.

Fast protein liquid chromatography (FPLC) was carried on synthetic LDL complexes. FIG. 5 depicts the FPLC profile of the unfractionated complexes. The profile indicates that the majority of synthetic particles are between LDL and HDL in size; isolated human LDL and HDL were used as references. As can be seen in FIG. 6, the size of the major sLDL peak is intermediate between plasma LDL and HDL (used in this study as reference particles). This size is consistent with the protein to lipid ratio which is intermediate to that of LDL and HDL.

Overall, these studies indicate that not only is it possible to form reproducible synthetic particles, but it is feasible to create a particle with a small diameter (a nanoparticle) that still maintains an exposed LDLR binding domain. A particle in the size range between LDL and HDL (7.5-25.0 nm) is likely to have greater diffusion in GBM tumors using CED than the larger native LDL. The observation that CSF is known to possess particles 11-13 nm diameter (Roheim, P. S. et al., *Proc Natl Acad Sci USA* 76:4646-4649 (1979)) supporting the notion that a nanoparticles in this size range will be useful for local drug delivery to brain tumors.

Peptide 1: This is the 18-A chimeric peptide (class A motif) described above; its sequence is:

DWLKAFYDKVAEKLKEAFRLTRKRGLKLA.    (SEQ ID NO: 3).

Preliminary results indicate that ~60% of the 18-A chimera complexed with small lipid particles.

Peptide 2: This chimeric peptide consists of two 18-A sequences, one before and one after the LDLR binding domain, and separated by prolines, as shown:

(SEQ ID NO: 7)
DWLKAFYDKVAEKLKEAFPRLTRKRGLKPDWLKAFYDKVAEKLKEAF.

Prolines are inserted before and after the binding domain to provide flexibility of the domains.

Peptide 3: This chimeric peptide consists of the apoB100 LDLR binding domain with its native N- and C-terminal flanking sequences intact (described above) coupled to one 18-A peptide in the amino terminal end. The sequence of this peptide is as follows:

(SEQ ID NO: 8)
DWLKAFYDKVAEKLKEAFYKLEGTTRLTRKRGLKLATALS.

The apoB sequence alone has low lipid binding affinity.

Source of peptides. The synthetic peptides based on apoB residue 3352-3367 and amphipathic helices were synthesized by Biosynthesis, Inc., Lewisville, Tex. All chimeric peptides were capped in the N-terminus with an acetyl group and in the C-terminus with an amine to stabilize the peptide. Peptides have >95% purity. The peptides are stored frozen until used and then made up in saline-Tris buffer, pH7.2. The peptides used in these studies were freely soluble in this buffer.

Peptide-Lipid Characterization

Chimeric peptide association with lipid emulsions: The peptides above were investigated for their ability to form synthetic LDL nanoparticles in the size and density range of HDL (d 1.063-1.21 g/ml) since such particles are postulated to have optimal diffusion under conditions of convection-enhanced delivery. The method described by Baille et al. (Baillie, G. et al., *J Lipid Res* 43:69-73 (2002)) was used with some modifications. The method that was developed based on preliminary studies (based on a PL:TO:CO mole ratio of 3:2:1) is as follows: lipids consisting of 11.25 mg egg yolk phospholipid (PL), 8.73 mg triolein (TO) and 3.21 mg cholesterol oleate (CO) are placed in a tube and evaporated to dryness under $N_2$. Six ml of Tris-saline buffer, pH 7.2, is added and the lipids are vortexed for 1 min and BHT, 20 µM, is added to the solution. The lipid emulsion is sonicated on ice for 1 hr and subsequently titanium particulates are removed by centrifugation (20 min, 4,000 rpm). The emulsion was extruded through a 0.1 micron polycarbonate filter at room temperature using the Avanti miniextruder and then through a 0.03 micron filter. To complex the peptide with the lipid emulsion, 1.27 mg peptide/ml lipid emulsion was incubated with the lipid at room temperature for 30 min. Unlike the Baille procedure where the apoB peptide used is hydrophobic and requires DMSO for solubilizing the peptide, no DMSO is required for making the complexes.

Isolation of synthetic LDL and other lipoprotein-like complexes from peptide-stabilized micro-emulsions: Studies have demonstrated that the peptide stabilized microemulsion, i.e., synthetic LDL, is not a single population of particles. To determine the distribution of lipid complexes in various density classes, sequential ultracentrifugation techniques were employed (Lindgren, F. T. et al., *In Blood Lipids and Lipoproteins: Quantification, Composition and Metabolism* (Nelson, G. J., ed.) pp. 181-274, John Wiley, New York (1972)); this preparative procedure is routinely used in our laboratory and is the classical method for isolation of LDL and other lipoproteins. The first centrifugation was performed at d 1.006 g/ml to isolate large lipid complexes with little peptide; the second spin was done at 1.006-1.063 g/ml to isolate particles in the LDL.size and density range; the third spin at d 1.063-1.21 g/ml isolates particles in the HDL size and density range. The d>1.21 g/ml fraction was isolated to assess how much of the peptide is in the lipid-poor form. All ultracentrifugal isolations use the Beckman TL100 ultracentrifuge for rapid isolations (all fractions can be obtained within 24 hr). The ultracentrifugation procedure can be confirmed by column chromatography techniques, such as fast protein liquid chromatography.

Characterization of synthetic lipoprotein particles: Ultracentrifugal and/or chromatographically isolated synthetic lipoproteins are fully characterized regarding their size, morphology and composition.

(1) Size and morphology: Particles in the LDL and HDL density range are evaluated by electron microscopy using the negative staining technique (Forte, T. M. et al., *Methods Enzymol* 128:442-457 (1986)).

(2) Composition: Peptide concentration are estimated by bicinchoninic acid assay using the Pierce BCA kit that measures proteins as small as 1,000 MW; enzyme endpoint kits (Wako) are used for triglyceride, cholesterol and phospholipid analyses.

The fully characterized synthetic lipoproteins are used to evaluate LDLR binding and uptake. Synthetic complexes exhibiting high recovery of the peptide on lipoprotein-like particles 20 nm or less in diameter and that recognize the antibody to LDLR binding domain are used for binding studies.

Example 3

Evaluation of the Targeting of the Synthetic LDL to GBM Cells In Vitro

It was hypothesized that small, synthetic LDL-like particles can recognize the LDLR on GBM cells and can bind the LDLR with high affinity and be internalized. Synthetic LDL nanoparticles were incubated with the SF-767, U-251 MG and SF-763 GBM cell lines that express different numbers of LDLRs to assess dose response of LDLR binding and uptake.

LDLR Binding Studies

Cell culture: The SF-767 cells (grade IV human glioblastoma) obtained from the Brain Tumor Research Center, University of California, San Francisco was used. This cell line was previously used by us to determine uptake of boronated protophoryphins into tumor cells (Callahan, D. E. et al., *Int J Radiat Oncol Biol Phys* 45:761-771 (1999)) and for assessing LDL binding affinity to LDLR (Maletinska, L. et al., *Cancer Res* 60:2300-2303 (2000)). A previously described protocol was used for cell culture techniques (Callahan, D. E. et al., *Int J Radiat Oncol Biol Phys* 45:761-771 (1999)). Essentially, cells in 2 chamber LabTek slides were grown in Eagle's MEM supplemented with 10% fetal bovine serum in the presence of 1% fungizone and 20 mg/L gentimicin. Twenty-four hrs before carrying out LDL binding studies, cells were switched to lipoprotein deficient (LPDS) medium.

Lipid labeling of synthetic and native LDL: The procedure essentially as described by Pitas et al. (Pitas, R. E. et al., *Arteriosclerosis* 1:177-185 (1981)) was used. The fluorescent lipid label, 3,3'-dioctadecylindocarbocyanine (DiI) (Molecular Probes) was used; 30 μl of DiI stock (3 mg/ml in DMSO) was added to 1 mg synthetic or plasma LDL and incubated 8 hr at 37° C. in the dark. Excess DiI was removed by centrifugation and filter sterilized. All sample handling was carried out under reduced lighting conditions.

Cell surface binding of DiI labeled synthetic and native LDL to GBM cells. To examine binding of synthetic LDL to LDLR on the surface of the cells, the cells were first chilled to 4° C. and then DiI labeled synthetic LDL was added at a concentration of 1.5 μM peptide per ml medium. Native LDL was added at a concentration of 5 μg protein per ml. Particles were incubated with cells for 3 hr and then cells are fixed and examined by fluorescence microscopy. As shown in FIG. 6A, using fluorescence microscopy, it was observed that that synthetic LDL binds to the surface of SF-767 cells in a punctate fashion indicative of binding to cell surface LDLR. Native LDL, labeled with DiI seen in FIG. 6B, was also shown to similarly bind to cell surfaces.

Fluorescence Microscopy: Two human GBM cell lines, SF-767 and U-251 were used. GBM cells were plated on 2-well chamber slides. The fluorescent lipid marker, DiI (red fluorescence) was introduced into synthetic and native LDL during 8 hr, 37° C. incubation. The FITC label (green fluorescence) bound to the N-terminus of the peptide was used as a fluorescent marker for the peptide. Prior to microscopy, cells were fixed with paraformaldehyde and cell nuclei were stained with DAPI (blue fluorescence).

Binding of $^{125}$I-labeled particles to GBM cells: Exponentially growing SF-767 cells are seeded into 35 mm wells at approximately $1 \times 10^5$ and allowed to grow for 3 days and followed by rinsing the cells with PBS and providing them with lipoprotein deficient serum (LPDS) (10% LPDS, 25 mM Hepes and 50 mg/L gentimicin in MEM). On day 4 when cells are 60-80% confluent, the binding studies are initiated. The binding studies are carried out at 4° C. essentially as described by Innerarity et al. (Innerarity, T. L. et al., *Methods Enzymol* 129:542-564 (1986)). Cells are pre-cooled on ice for 15 min and then cell medium is replaced with chilled LPDS medium containing varying concentrations of labeled LDL or synthetic lipoproteins. Cholesterol concentration is used for standardizing additions because of the disparity in molecular weights between apoB100 and peptide. To evaluate non-specific binding, 50-fold excess of unlabeled native LDL or synthetic particles is used in several dishes. After 4 hr incubation the medium is removed and cell monolayer solubilized after careful rinsing. Cells are solubilized with 0.3 M NaOH, protein determined by the modified Lowry assay (Markwell, M. K. et al., *Anal Biochem* 87:206-210 (1978)) and $^{125}$I labeled LDL binding is determined by gamma counting. The difference between total and nonspecific binding provides information on the saturable specific binding of LDL or synthetic LDL to cells. Scatchard analysis is carried out on native LDL and all synthetic LDL particles to determine $K_d$ and $B_{max}$. These data provide the necessary information on the chimera peptide affinity for the LDLR and an estimate on the amount of label bound to the surface of cells. These experiments are designed to elucidate which synthetic lipoprotein(s) (LDL nanoparticle) has the highest cell binding capacity.

Figure 7:
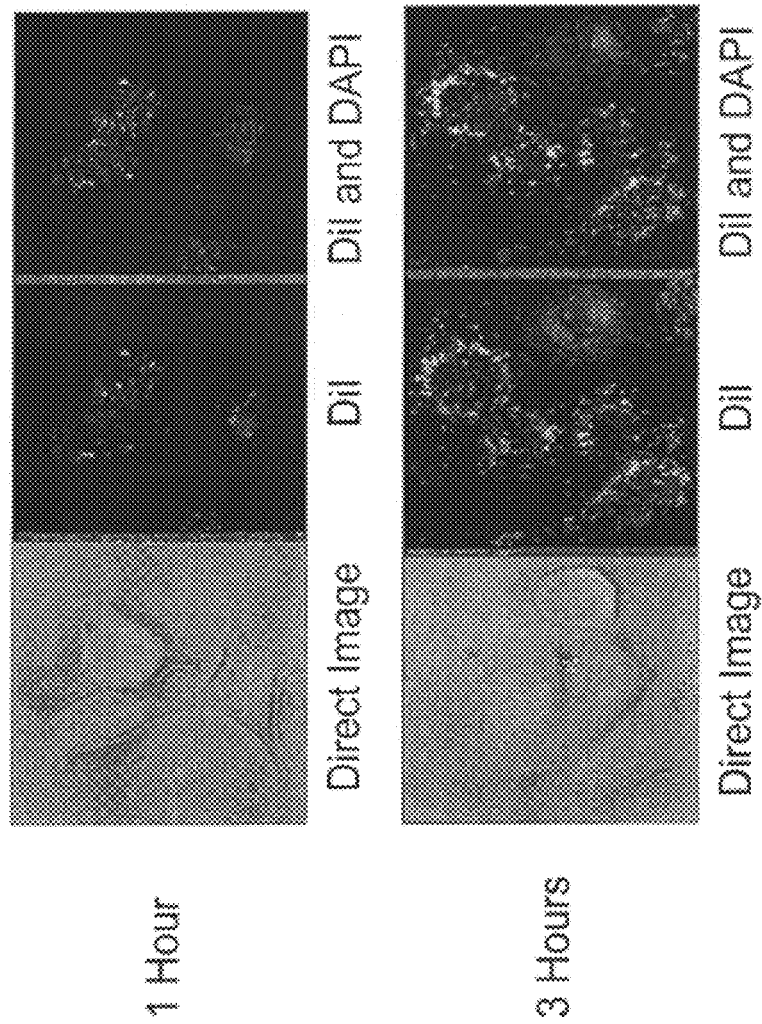
FIG. 7 depicts cell uptake at 37° C. (1.5 μM peptide) of fluorescently labeled (DiI) sLDL at 3 hours as compared to 1 hour. Fluorescence was perinuclear. Time dependency of sLDL uptake suggests that sLDL endocytosis is receptor mediated.
Figure 8:
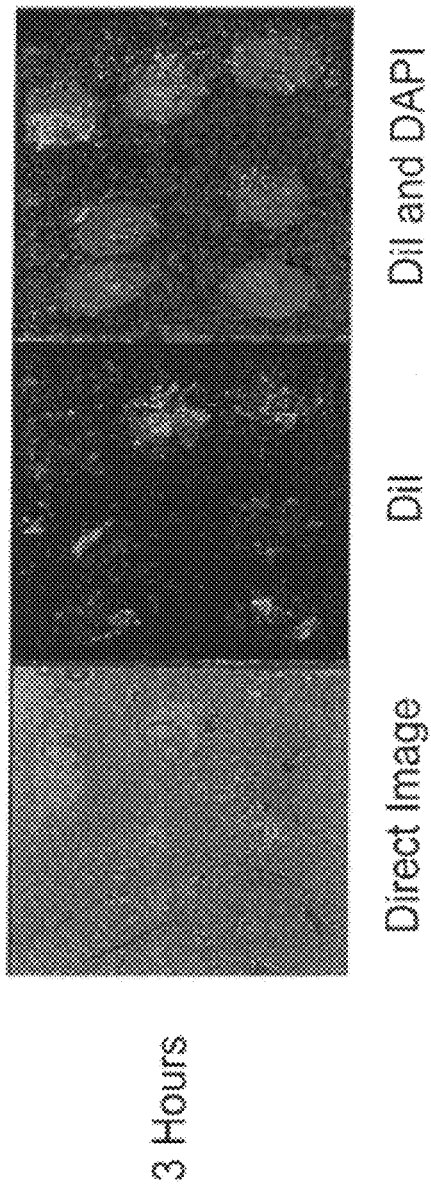
FIG. 8 depicts cell uptake and localization of fluorescently labeled (DiI) native LDL. Label distribution is similar to that of synthetic LDL. Cell uptake was carried out at 37° C., 3 hr (10 μg protein/mL).

Internalization of DiI labeled synthetic LDL: The lipid moiety of synthetic LDL using the bifunctional peptide consisting of the 18 a.a. amphipathic alpha helix and the LDLR binding domain was labeled with DiI according to the method of Pitas et al. (Pitas, R. E. et al., *Arteriosclerosis* 1:177-185 (1981)), hereby incorporated by reference. Exponentially growing SF 767 cells are used and grown in 10% LPDS for 24 hr before the introduction of labeled lipoprotein particles. The DiI labeled synthetic LDL (1.5 μM peptide) was incubated with SF-767 cells at 37° C. for 1 or 3 hr and then evaluated by fluorescence microscopy. The SF-767 cells in FIG. 7 exhibited internalized lipid after 3 hr incubation with DiI-labeled synthetic LDL. This uptake is similar to that of native LDL (10 μg/ml) labeled with DiI as seen in FIG. 8. The 1 hr incubation also showed internalization of DiI labeled LDL but the amount of label within the cell was less indicating that uptake is time dependent.

Figure 9:
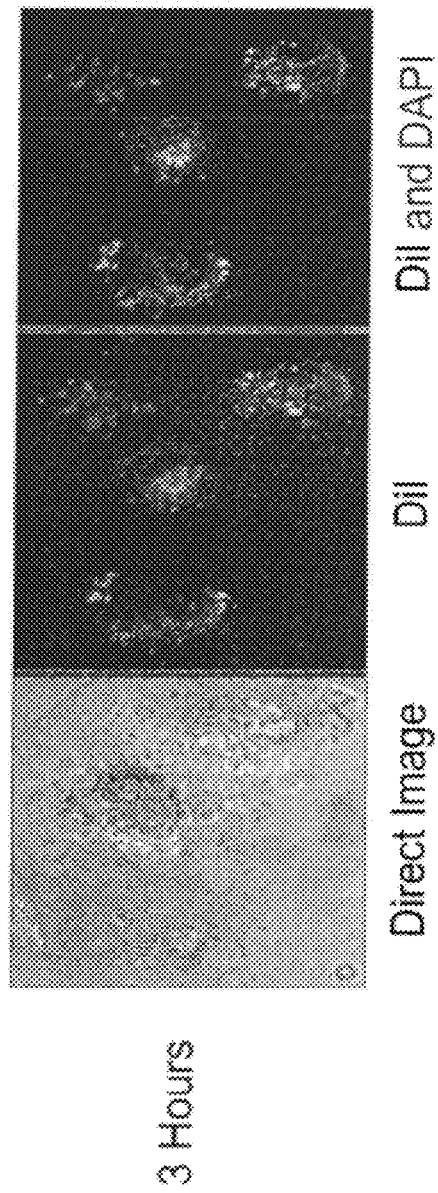
FIG. 9 depicts uptake of fluorescently labeled (DiI) synthetic LDL by U-251 cells indicating that sLDL uptake is not unique to SF-767 cells. Cell uptake was carried out at 37° C., 3 hr (1.5 μM peptide).

Uptake of DiI labeled synthetic LDL by U-251 cells: This cell line was tested for uptake of DiI labeled synthetic LDL to demonstrate that LDLR uptake of synthetic LDL is not specific for the SF-767 cells and to demonstrate that there is uptake into GBM cells that have lower numbers of LDLR. FIG. 9 shows a fluorescent microscope image of U-251 cells taken after incubation of cells with DiI labeled synthetic LDL for 3 hr at 37° C. Synthetic LDL uptake is considerable at this time point.

Co-localization of peptide and lipid in SF-767 cells: Another consideration was that peptide and lipid co-localize in the cell indicating that the synthetic LDL was endocytosed intact into the cell. To accomplish this, the peptide was labeled with a fluoroscein label (FITC) at the N-terminus. The FITC labeled peptide was incorporated into the lipid emulsion and after dialysis of the complexes the synthetic LDL were labeled with DiI. SF-767 grown as above were exposed to 15 μM peptide for up to 6 hr and then fluorescent microscopy carried out with the appropriate filters. FIG. 10 shows FITC (green fluorescence) and DiI (red fluorescence) localization. The images were merged and reveal that the peptide and lipid co-localize. This suggests that the synthetic LDL remain intact upon entry into the cell.

Internalization of iodinated synthetic LDL: Internalization is determined using the procedure of Goldstein et al. (Goldstein, J. L. et al., *Methods Enzymol* 98:241-260 (1983)). SF-767 cells grown in 35 mm dishes are incubated with the $^{125}$I-labeled particles at 37° C. for 3 hr. Surface bound label can be accounted for by chilling cells and treating the culture with 10 mg/ml heparin (1 hr) to release surface associated radioactivity. Washed cells are solubilized and radioactivity quantified by gamma counting. Native LDL is used as a reference for the technique. It is expected that the U-251 MG cells will have reduced uptake since it has previously been shown that this cell line has approximately one-half the number of LDLR as SF-767.

Statistical analysis: Binding studies are carried out at least three times. Differences in LDLR binding and LDL internalization between synthetic LDL with different peptides and native LDL are evaluated by ANOVA. Significance is indicated by $p<0.05$.

Additional considerations: It has previously been shown that the LDL receptor number on stage IV GBM is variable (Maletinska, L. et al., *Cancer Res* 60:2300-2303 (2000)); some cells have exceedingly high numbers and others have intermediate and low numbers. SF-767 has intermediate numbers of receptors (288,000) while U-251 MG has low numbers (128,000). The SF-763 line, on the other hand, has extremely high numbers of receptors (950,000). To ascertain that uptake of synthetic LDL is consistent with receptor number; a series of binding and uptake studies were carried out with the SF-763 cells and compared with those of SF-767 and U-251.

Intracellular Localization of Synthetic LDL

It is fully expected that synthetic lipoproteins internalized via the LDLR would be processed like a native LDL and therefore appear in the lysosomes. This was tested by using fluorescent tags, one specific for lysosomes and the other for synthetic LDL, and examining the cells by fluorescent microscopy.

Culturing GBM cells: SF-767 cells were grown on sterile glass coverslips as previously described (Callahan, D. E. et al., *Int J Radiat Oncol Biol Phys* 45:761-771 (1999)). Essentially $4 \times 10^5$ cells were placed in 60-mm dishes containing the cover slips and allowed to grow to approximately 60% confluency. One day before imaging the conditioned medium was removed, cells rinsed and medium replaced with LPDS (10%) containing fluorescent labeled synthetic LDL or native LDL.

Labeling synthetic LDL and lysosomes: The synthetic LDL was be labeled with the lipophilic fluorescent marker, 3',3'-dioctodecylinodarbocyanine (DiI) (Molecular Probes, OR), essentially as described by Pitas et al. (Pitas, R. E. et al., *Arteriosclerosis* 1:177-185 (1981)). DiI-labeled native LDL and synthetic LDL was introduced into the medium at a concentration of 5-7 µg/ml cholesterol and incubated at 37° C. for 3 hr. Following incubation, the cells were washed with PBS containing 2 mg/ml bovine serum albumin and then fixed for 30 min with 3% formalin in phosphate buffer at room temperature. Distribution of DiI was assessed by fluorescence microscopy. It was expected that the labeled LDL and synthetic LDL would accumulate in the lysosomes. Lysosomal localization was verified by co-localization of the dye, Lysotracker Red, LT-red, (Molecular Probes, OR) that selectively labels lysosomes. A minimum of five images (15-35 cells per image) from five different areas on the coverslip were obtained. Laser confocal microscopy using the Bio-Rad MRC-104 laser confocal microscope was used to verify the intracellular distribution of the DiI and LT-red in unfixed cells. These fluorescence microscopy studies were aimed at providing information as to whether the synthetic lipoproteins bearing the LDLR binding domain have the same cellular distribution as native LDL.

Additional considerations: To confirm that the synthetic lipoproteins are bound and internalized via the LDLR, several approaches were used. Approach #1: carry out binding studies at 4° C. to localize surface LDLR. Cells were chilled and after washing with cold LPDS, fresh cold LPDS with DiI-labeled synthetic or native lipoproteins were added and incubated at 4° C. for 3 hr. The cells were then rinsed, fixed in formalin at 4° C. for 15 min and then examined for surface distribution of the label by fluorescence microscopy. Approach #2: block DiI-labeled synthetic lipoprotein binding and uptake by incubating cells with a 50-fold excess of unlabeled particles and/or LDL and incubate for 3 hr at 37° C. Approach #3: treat cells with antibody to LDLR. Approach #4: treat cells with suramin which blocks interaction between the ligand and LDLR.

Co-localization of peptide and lipid in lysosomes: The representative images in FIG. 20 A and FIG. 20 B were obtained from cells fixed after 3 hours incubation of cells with dual labeled sLDL nanoparticles (1.5 µM peptide) where the peptide carried the FITC label and lipid the DiI label. FIG. 20 A depicts FITC label of peptide and FIG. 20 B depicts DiI label in lipids. The representative images in FIG. 20 C through F were obtained from living SF-767 cells after 1 hour incubation with dual labeled sLDL nanoparticle (1.5 µM peptide). FIG. 20 C depicts FITC-labeled peptide; FIG. 20 D depicts DiI-labeled lipids; FIG. 20 E depicts images in C and D merged to show co-localization of peptide and lipid; FIG. 20 F depicts Lysotracker Blue image for localization of lysosome revealing co-localization of the peptide and lipid in lysosomes.

Figure 11B:
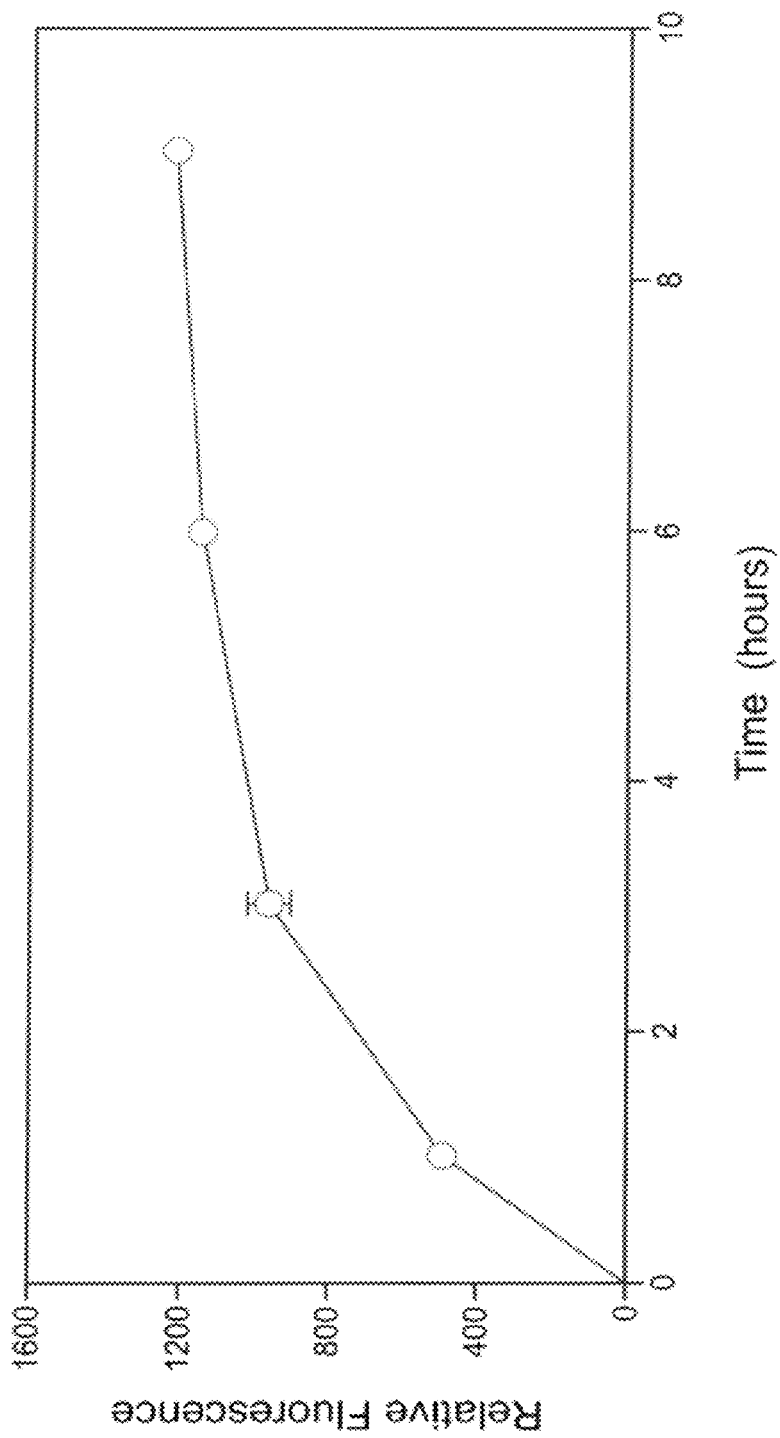
FIG. 11 depicts that synthetic LDL nanoparticle uptake by SF-767 cells is time and concentration dependent.

Uptake of synthetic LDL nanoparticles is time and concentration dependent: As shown in FIG. 11, synthetic LDL nanoparticle uptake by SF-767 cells is time and concentration dependent. FIG. 11. A uses fluorescence microscopy to show that uptake of DiI-labeled synthetic LDL is time dependent. Uptake of DiI-labeled lipids was tested at 1, 3, 6 and 9 hours. SF-767 cells were fixed with 4% paraformaldehyde at each time point prior to microscopy. The experiment was repeated with separately produced batch of synthetic LDL and yielded identical results. FIG. 11. B shows FACS analysis the data of which indicate that uptake of DiO-labeled synthetic LDL is time-dependent. SF-767 cells were incubated for 1, 3, 6, and 9 hours at 37° C. with the synthetic LDL particles previously labeled with DiO. Data represents mean+/−standard deviation of three separate wells. FIG. 11. C shows the results of FACS analysis showing that uptake of DiO-labeled synthetic LDL particles is concentration dependent. Cells were incubated for 3 hours at 37° C. with varying concentrations of synthetic LDL particles (0.1, 1, 5 and 10 µM peptide) that had been previously labeled with DiO. Data represents mean+/−standard deviation of three separate wells. This experiment was repeated two additional times with separate synthetic LDL batches and yielded identical results.

Uptake of DiO-labeled synthetic LDL nanoparticles is dependent on LDL receptor number: FIG. 11 shows the dependence of sLDL nanoparticle uptake on the levels of LDLR expression. SF-763 cells and SF-767 cells, both of which have higher levels of expression of LDLR than U-251 cells show higher accumulation of sLDL nanoparticles, than U-251. Cells were incubated for 3 hours at 37° C. with synthetic LDL (1.5 µM peptide) previously labeled with DiO. At the conclusion of the experiment, cells were trypsinized and resuspended in PBS. Data for each cell line represents the mean+/−standard deviation of three separate wells. This experiment was repeated using a separate batch of synthetic LDL and yielded similar results Example 4

Paclitaxel Oleate Loading Unto Synthetic LDL Nanoparticles and Evaluation of Cell Killing In Vitro Paclitaxel is a chemotherapeutic which promotes the polymerization of tubulin. The microtubules formed in the presence of paclitaxel are extraordinarily stable and dysfunctional, thereby causing cell death by disrupting the normal tubule dynamics required for cell division and vital interphase processes. Paclitaxel oleate (PO) is a lipophilic derivative of paclitaxel first described by Lundberg et al. Paclitaxel oleate (PO) was constructed by combining paclitaxel with oleoyl chloride. The product was purified by flash column chromatography and identified by thin-layer chromatography. The identity of the product was verified by nuclear magnetic resonance on a Bruker Avance 300 MHz NMR instrument (UC Berkeley). To quantify PO, a reverse phase high-performance liquid chromatography (HPLC) protocol was developed. PO was found to have an 11 minute retention time on a C-18 column in 100% acetonitrile at a flow rate of 1.0 mL/min (227 nm). Paclitaxel oleate was added to the initial microemulsion mixture in a ratio of 3:2:1:0.5 (PC:TO:CO:PO). The final microemulsion was centrifuged and dialyzed against Tris-saline buffer. The microemulsion was run through the HPLC and compared to PO standards. These preliminary studies indicate that by using this lipid to drug ratio, 48±3% of the initial PO added remained bound to the microemulsion after processing. The sLDL particle containing paclitaxel oleate is heretofore referred to as "sLDL-PO".

Figure 13:
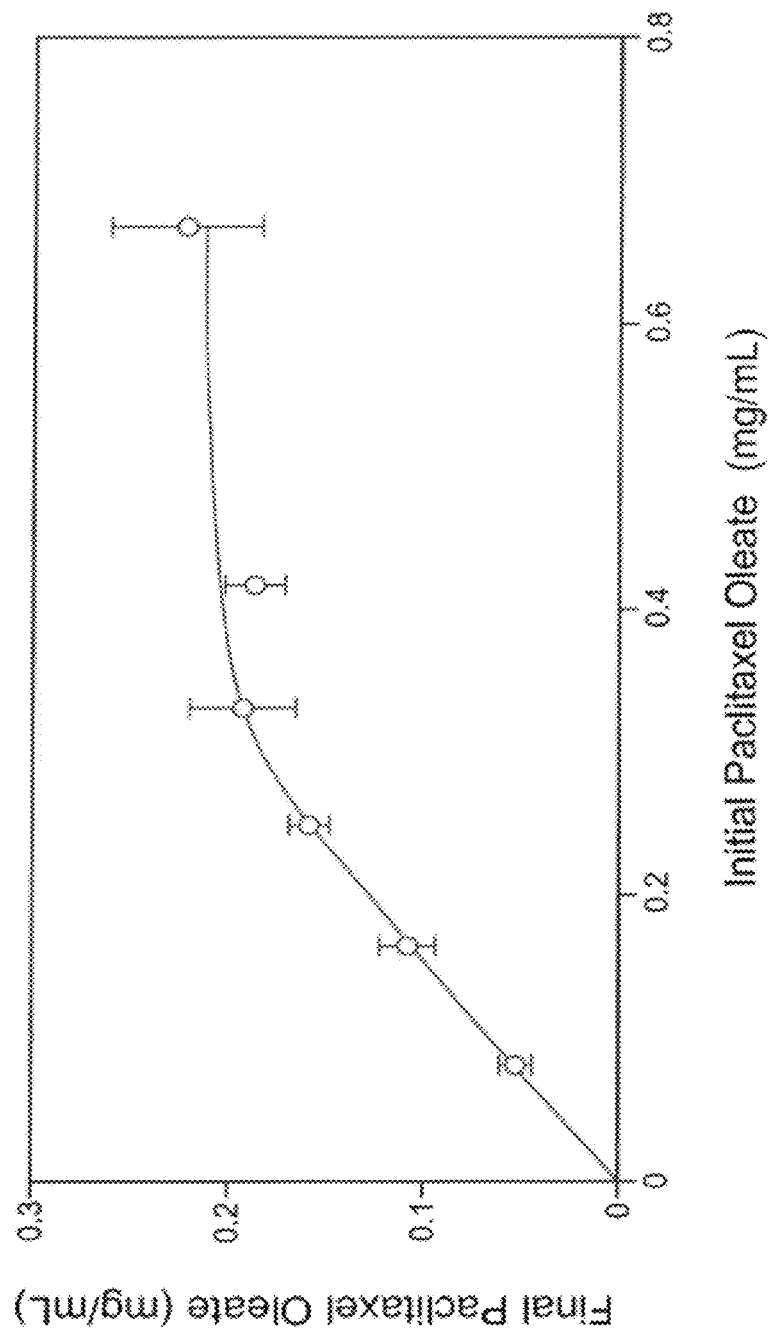
FIG. 13 depicts Paclitaxel oleate (PO) content of microemulsions with different starting amounts of paclitaxel oleate. Paclitaxel oleate amounts were quantified by reverse phase HPLC. Each data point represents the mean+/−standard deviation of three separate microemulsions.
Figure 15A:
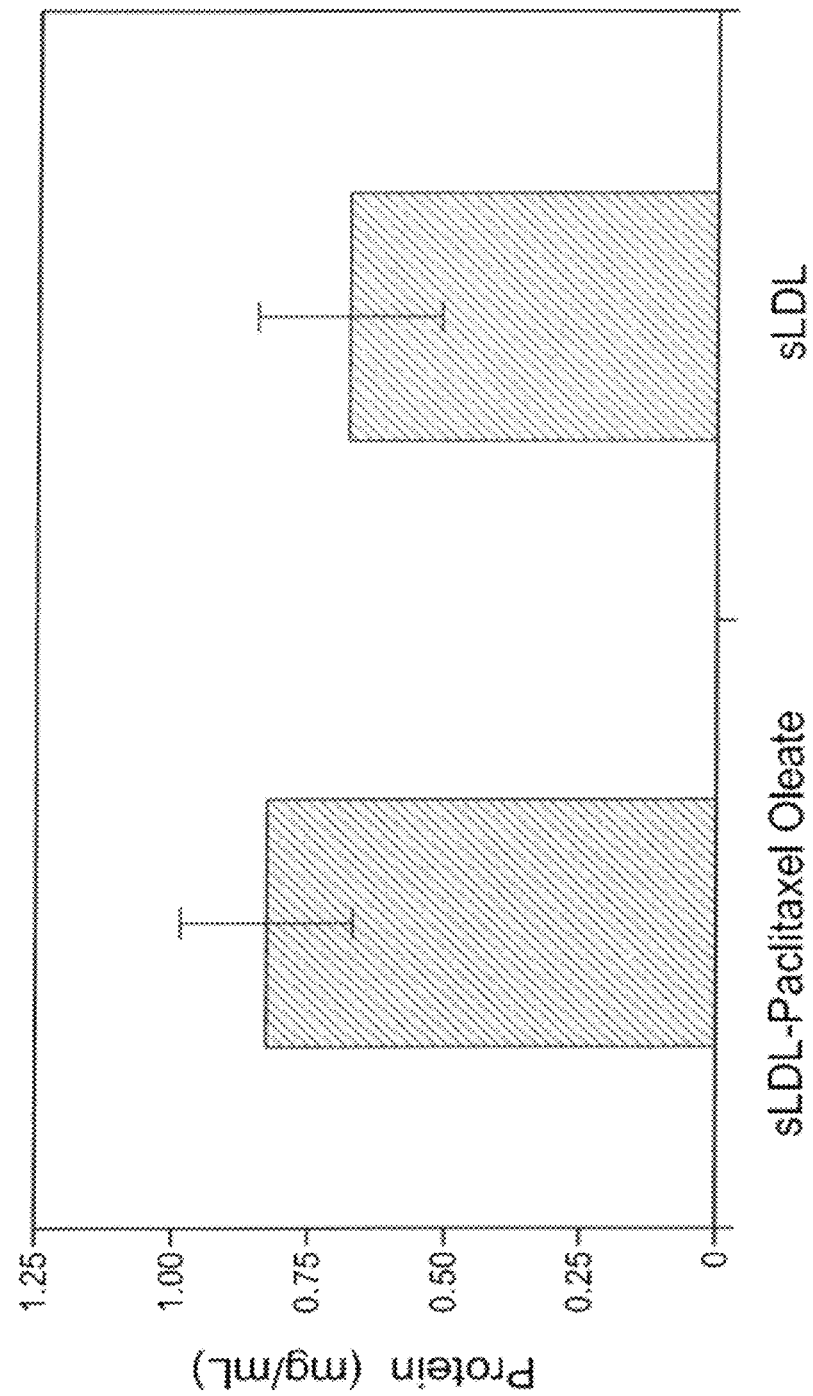
FIG. 15. A depicts that Synthetic LDL (sLDL) constructed with and without paclitaxel oleate have the same protein amounts.
Figure 15B:
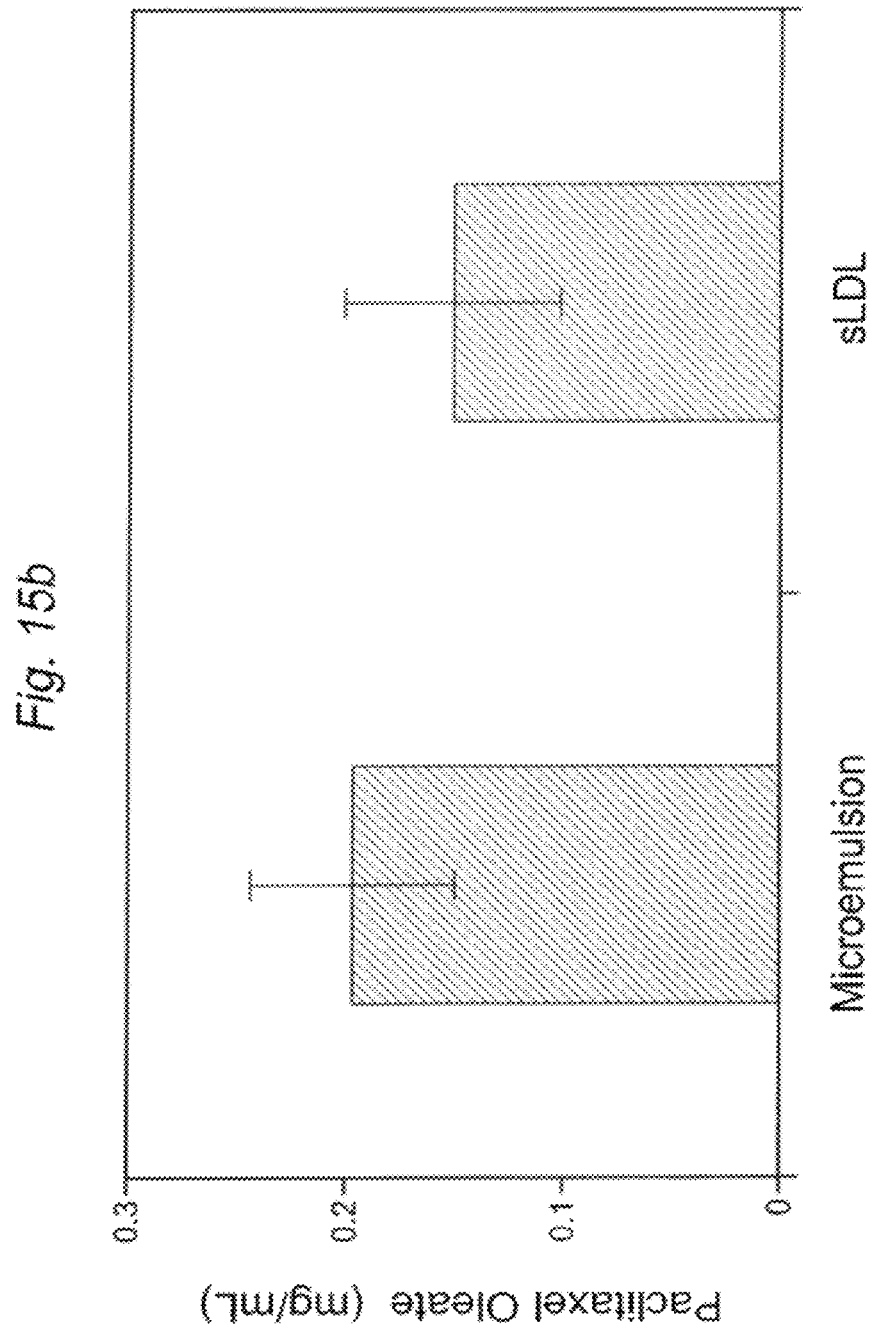
Figure 16:
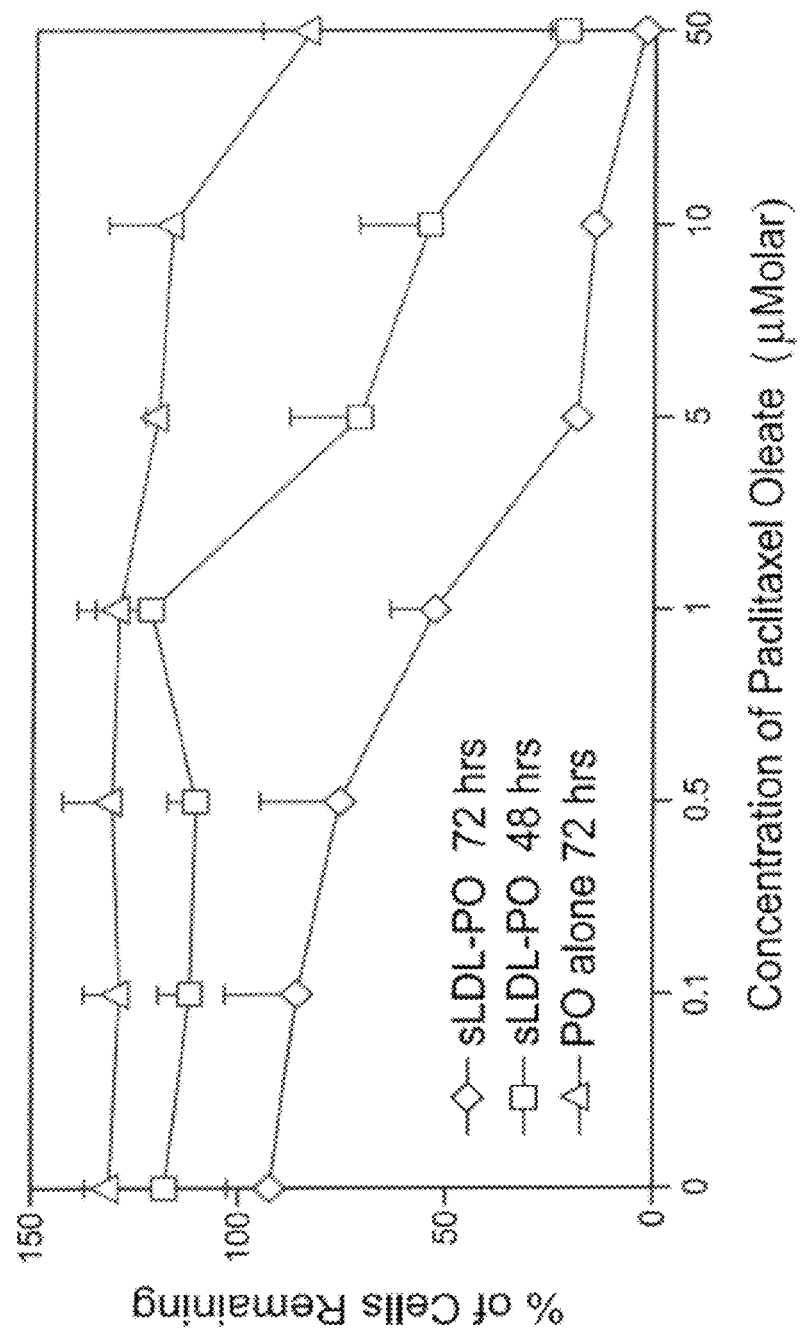
FIG. 16 depicts that synthetic LDL containing paclitaxel oleate (sLDL-PO is capable of killing HeLa cells. $IC_{50}$, the concentration required to kill half of the cells, is approximately 1 µM (sLDL-PO, 72 hr) and 10 µM (sLDL-PO, 48 hr). Data represent the mean+/−standard deviation of three separate wells. Paclitaxel oleate alone is ineffective in HeLa cell killing in concentrations up to 50 µM.
Figure 17:
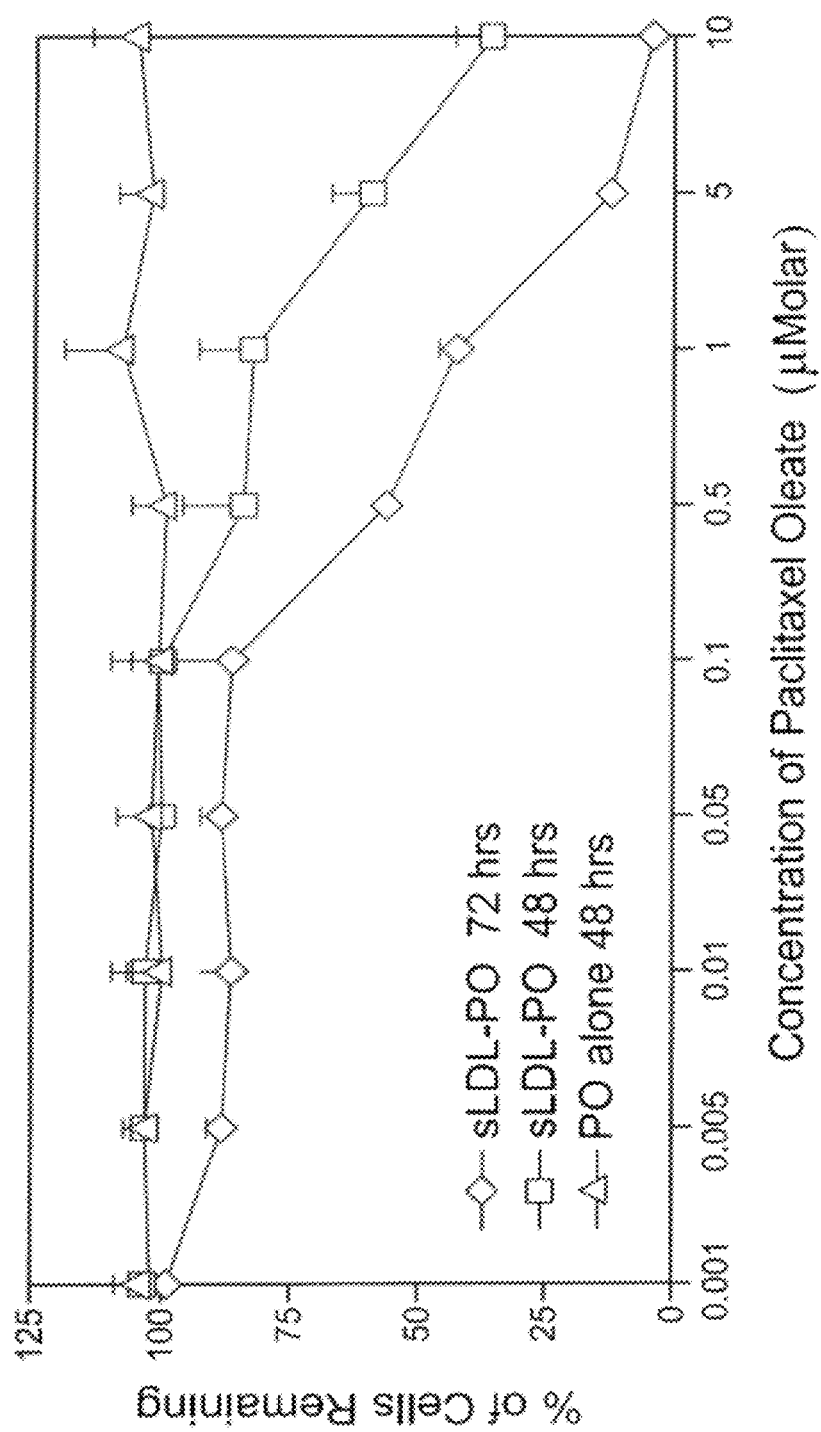
FIG. 17 depicts that synthetic LDL containing paclitaxel oleate (sLDL-PO) is capable of killing SF-767 cells. $IC_{50}$ are approximately 0.7 µM (sLDL-PO, 72 hr) and 7 µM (sLDL-PO, 48 hr). Data represent the mean±SD of three separate wells. Paclitaxel oleate alone is ineffective in concentrations up to 10 µM.

To demonstrate that PO can be incorporated into lipid microemulsions, PO was added to the initial lipid mixture in varying concentrations and the final amount of PO incorporated was quantified as shown in FIG. 13. Paclitaxel oleate incorporation appears to saturate around 0.33 mg/mL PO. This initial PO concentration was used for further studies to determine whether there was a difference in the incorporation of PO vs. underivatized paclitaxel. FIG. 14A demonstrates a 4-5 fold increase in incorporation for paclitaxel oleate as compared to paclitaxel. FIG. 14B demonstrates the PO incorporation is not affected by the presence of cholesteryl oleate. As such, the cholesteryl oleate was not included in all future microemulsions. FIG. 15A demonstrates that the presence of PO does not affect the ability of the peptide to bind to the microemulsion to form a synthetic LDL which indicates that the PO incorporates into the core of the particle. FIG. 15B demonstrates that when the peptide is added to construct the synthetic LDL, the PO content is not altered.

sLDL-PO was added to HeLa cells as shown in FIG. 16 and to SF-767 glioblastoma multiforme tumor cells (shown in FIG. 17) at concentrations between 0.05 and 50 µM and cell killing was determined by the MTT assay. In both cell lines, sLDL-PO demonstrated significantly better cell killing than PO alone. Cell killing was significantly higher after 72 hrs as compared to 48 hrs for both cell lines. These results demonstrate that sLDL-PO is capable of cell killing and provides an improvement over PO alone.

Figure 18:
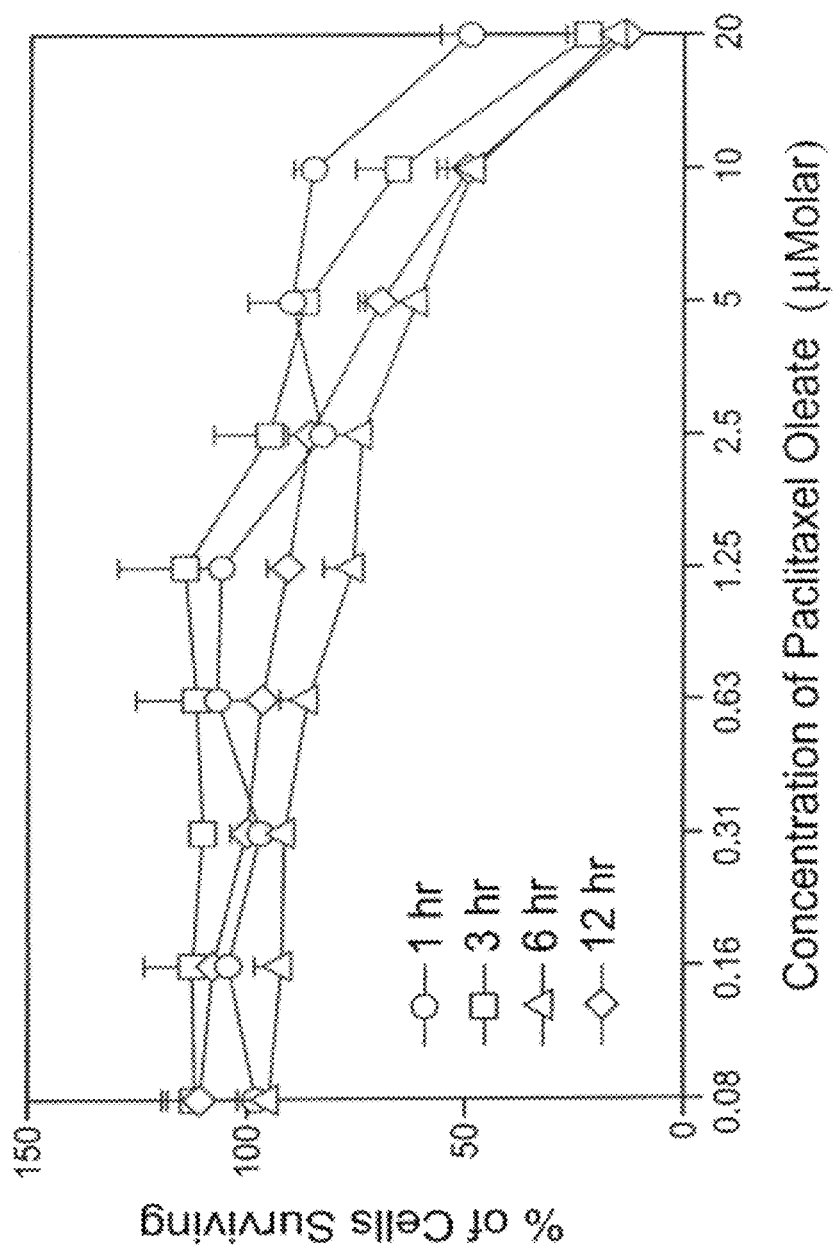
FIG. 18 depicts the effect of time and concentration synthetic LDL containing paclitaxel oleate (sLDL-PO) cell killing. SF-767 cells were incubated with sLDL-PO for varying times (1, 3, 6, 12 hrs) after which the sLDL-PO was removed and fresh media without drug was added to cells for a 72 hr total incubation. $IC_{50}$ values were: 20 µM (1 hr), 15 µM (3 hr), 10 µM (6 hr), and 10 µM (12 hr). The plateau in cell killing at 12 hr indicates saturation in uptake which is characteristic of receptor mediated endocytosis by LDLR. The data also indicate that shorter incubation times with the sLDL-PO will also result in cell killing. A shorter incubation time with the sLDL-PO is likely to be more representative of an in vivo treatment. Data represent the mean+/−standard deviation of three separate wells.
Figure 19:
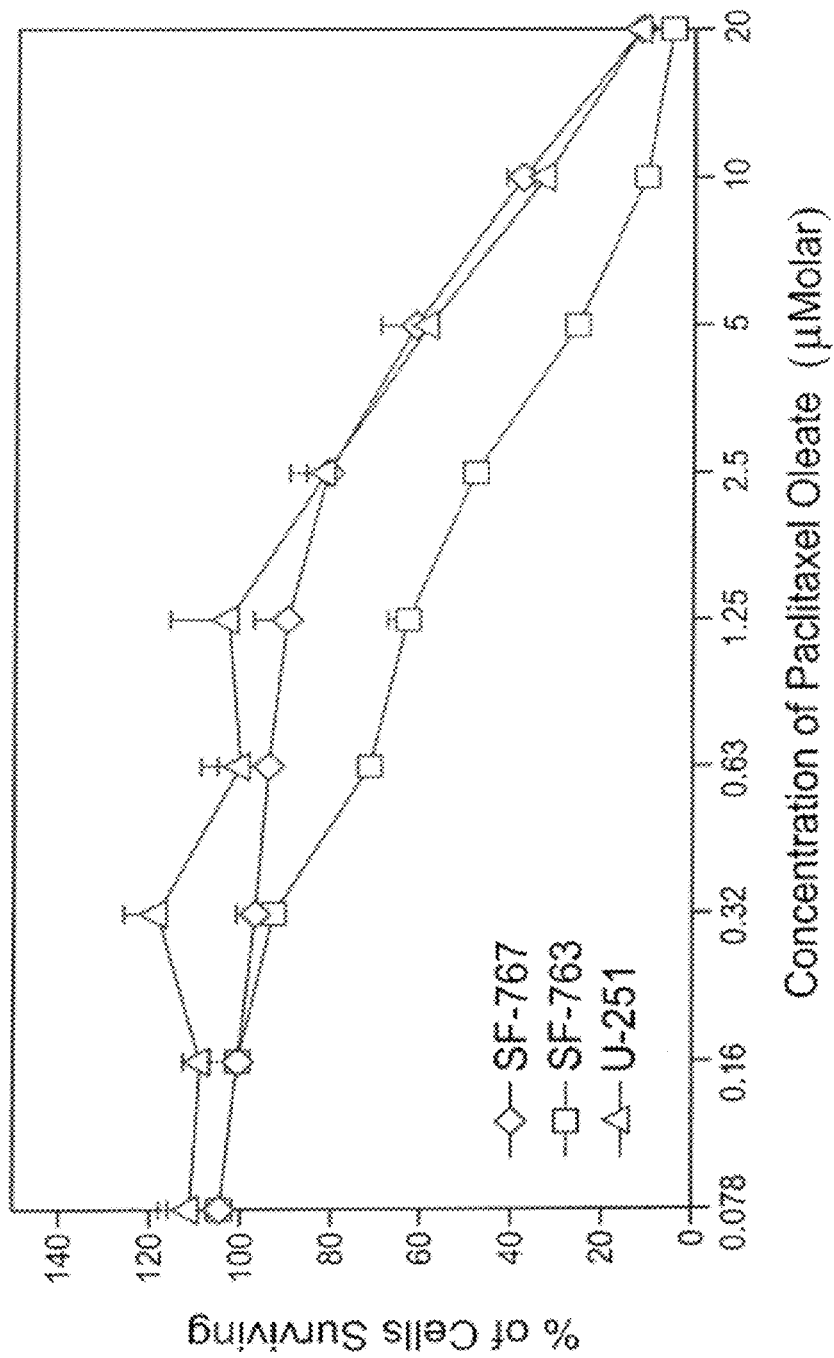
FIG. 19 depicts the effect of sLDL-PO on different GBM cell lines. GBM cells expressing high numbers of LDL receptors (SF-767, SF-763, and U-251) were incubated with sLDL-PO for 6 hrs after which the sLDL-PO was removed and fresh media without drug was added to cells for a 72 hr total incubation; $IC_{50}$ values were: 7 µM (SF-767), 2 µM (SF-763), and 7 µM (U-251). These results demonstrate that sLDL-PO is capable of killing cells possessing LDL receptors. Data represent the mean+/−standard deviation of three separate wells. This experiment was repeated with a separately derived batch of sLDL-PO and yielded identical results.

FIG. 18 shows that the dependence of cell survival is dependent on the concentration of Paclitaxel Oleate and that survival is a function of time. Cells were grown as in Example 3. As shown in FIG. 19, cell survival in dependent on paclitaxel oleate concentration in SF-767, U-251, and SF-763 cell medium. These data show that sLDL-PO particles can kill tumor cells with varying LDLR numbers.

---

What is claimed is:

1. A synthetic LDL nanoparticle comprising a lipid moiety and a synthetic chimeric peptide, wherein:
the lipid moiety forms a particle of about 10-30 nm in size, and
the synthetic chimeric peptide comprises an amphipathic α-helix and an LDL receptor binding domain, wherein the LDL receptor binding domain consists of the following amino acid sequence:

$(R^1)_x$-Arg-Leu-Thr-Arg-Lys-Arg-Gly-Leu-Lys-$(R^2)_y$ in which
$R^1$ is an amino acid sequence from 1 to 40 amino acids wherein each amino acid is independently selected from the group consisting of naturally occurring amino acids and amino acid mimetics;
$R^2$ is an amino acid sequence from 1 to 40 amino acids wherein each amino acid is independently selected from the group consisting of naturally occuring amino acids and amino acid mimetics; and
x and y are independently selected and are equal to zero or one (SEQ ID NO:9).

2. The synthetic LDL nanoparticle of claim 1, wherein the mean LDL nanoparticle size is about 10 nm.

3. The synthetic LDL nanoparticle of claim 1, wherein the lipid moiety comprises a microemulsion of lipids selected from the group consisting of phospholipids, triglyceride, cholesteryl ester, and a combination thereof.

4. The synthetic LDL nanoparticle of claim 3, wherein the microemulsion comprises phospholipids, triolein and optionally cholesteryl oleate, wherein the molar ratio among the phospholipids, triolein and cholesterol oleate is selected from the group consisting of 3:2:1, 3:1:2, 3:0.5:2 and 3:2:0.

5. The synthetic LDL nanoparticle of claim 1, wherein the amphipathic α-helix comprises 10 to 22 amino acids.

6. The synthetic LDL nanoparticle of claim 5, wherein the amphipathic α-helix is selected from the group consisting of Segrest peptide, 18A peptide substituted with F3 and F4, ApoAI helix 9 and ApoAI helix 10.

7. The synthetic LDL nanoparticle of claim 1, wherein x and y are both zero (SEQ ID NO:1).

8. The synthetic LDL nanoparticle of claim 1, wherein:
x is one;
$R^1$ is Asp-Trp-Leu-Lys-Ala-Phe-Tyr-Asp-Lys-Val-Ala-Glu-Lys-Leu-Lys-Glu-Ala-Phe (SEQ ID NO:2);
y is one; and
$R^2$ is Leu-Ala.

9. The synthetic LDL nanoparticle of claim 1, wherein:
x is one;
$R^1$ is Asp-Trp-Phe-Lys-Ala-Phe-Tyr-Asp-Lys-Val-Ala-Glu-Lys-Phe-Lys-Glu-Ala-Phe (SEQ ID NO:10);
y is one; and
$R^2$ is Leu-Ala.

10. The synthetic LDL nanoparticle of claim 1, wherein:
x is one;
$R^1$ is Tyr-Lys-Leu-Glu-Gly-Thr-Thr (SEQ ID NO:11);
y is one; and
$R^2$ is Leu-Ala-Thr-Ala-Leu-Ser (SEQ ID NO:12).

11. The synthetic LDL nanoparticle of claim 1, wherein:
x is one;
$R^1$ is Pro-Ala-Leu-Glu-Asp-Leu-Arg-Gln-Gly-Leu-Leu-Pro (SEQ ID NO:13);
y is one; and
$R^2$ is Leu.

12. The synthetic LDL nanoparticle of claim 1, wherein:
x is one;
$R^1$ is Asp-Trp-Leu-Lys-Ala-Phe-Tyr-Asp-Lys-Val-Ala-Glu-Lys-Leu-Lys-Glu-Ala-Phe-Pro (SEQ ID NO:14);
y is one; and
$R^2$ is Pro-Asp-Trp-Leu-Lys-Ala-Phe-Tyr-Asp-Lys-Val-Ala-Glu-Lys-Leu-Lys-Glu-Ala-Phe (SEQ ID NO:15).

13. The synthetic LDL nanoparticle of claim 1, wherein:
x is one;
$R^1$ is Asp-Trp-Leu-Lys-Ala-Phe-Tyr-Asp-Lys-Val-Ala-Glu-Lys-Leu-Lys-Glu-Ala-Phe-Tyr-Lys-Leu-Glu-Gly-Thr-Thr (SEQ ID NO:16);
y is one; and
$R^2$ is Leu-Ala-Thr-Ala-Leu-Ser (SEQ ID NO:12).

14. The synthetic LDL nanoparticle of claim 1, wherein the chimeric peptide comprises two amphipathic α-helices.

15. The synthetic LDL nanoparticle of claim 1, wherein the synthetic LDL nanoparticle further comprises one or more therapeutic compounds.

16. The synthetic LDL nanoparticle of claim 15, wherein the therapeutic compound is selected from the group consisting of small organic molecules, radioisotopes, inorganic molecules, polypeptides, peptides, antibodies, siRNA, nucleic acids, bacterial toxins and a combination thereof.

17. The synthetic LDL nanoparticle of claim 15, wherein the therapeutic compound is taken up by the lipid moiety of the synthetic LDL nanoparticle or is covalently or non-covalently attached to the amphipathic α-helix of the chimeric peptide.

18. A method for treating or preventing a central nervous system disease in a patient, the method comprising the step of administering a therapeutically effective amount of a synthetic LDL nanoparticle comprising a lipid moiety and a synthetic chimeric peptide to the patient, wherein:

the lipid moiety forms a particle of about 10-30 nm in size, and the synthetic chimeric peptide comprises an amphipathic α-helix and an LDL receptor binding domain, wherein the LDL receptor binding domain consists of the following amino acid sequence:

$(R^1)_x$-Arg-Leu-Thr-Arg-Lys-Arg-Gly-Leu-Lys-$(R^2)_y$ in which
- $R^1$ is an amino acid sequence from 1 to 40 amino acids wherein each amino acid is independently selected from the group consisting of naturally occurring amino acids and amino acid mimetics;
- $R^2$ is an amino acid sequence from 1 to 40 amino acids wherein each amino acid is independently selected from the group consisting of naturally occuring amino acids and amino acid mimetics; and
- x and y are independently selected and are equal to zero or one (SEQ ID NO:9), and wherein the synthetic LDL nanoparticle further comprises one or more therapeutic compounds, thereby treating or preventing the disease.

19. The method of claim 18, wherein the method of administering the synthetic LDL nanoparticle is selected from the group consisting of systemic and local.

20. The method of claim 18, wherein the disease is cancer that occurs in the brain.

21. The method of claim 18, wherein the disease is selected from the group consisting of GBM, astrocytoma, ependymoma, medulloblastoma, oligodendrocytoma, meningioma, pituitary adenoma, neurilemmona, metastatic carcinoma, craniopharyngioma, dermoid, epidermoid, teratoma, angiomas, vascular malformations, sarcomas, pinealoma, chordoma, and granuloma.

22. The method of claim 18, wherein the central nervous system disease is selected from the group consisting of: stroke, epilepsy, head trauma, viral infection, bacterial infection, fungal, rickettsial, protozoan, or helminthic infections, Alzheimer's disease, Parkinson's disease, multiple sclerosis, and hereditary metabolic diseases of the brain.

23. The method of claim 18, wherein the therapeutic compound is selected from the group consisting of small organic molecules, inorganic molecules, therapeutic peptides and proteins, antibodies, radioisotopes, siRNA and nucleic acids for gene therapy, toxins, and anti-cancer agents.

24. The method of claim 23, wherein the anti-cancer agent is paclitaxel oleate, paclitaxel, or doxorubicin.

25. The method of claim 22 wherein the central nervous system disease is meningitis caused by picornavirus, togavirus, herpesvirus, paramyxovirus, or arenavirus; or HIV-associated cognitive dysfunction.

26. The method of claim 22, wherein the central nervous system disease is cryptococcal meningitis, fulminant bacterial meningitis, neurotuberculosis, toxoplasmosis, or neurosyphilis.

* * * * *

SEQUENCE LISTING

```
<160> NUMBER OF SEQ ID NOS: 16

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence:
      apolipoprotein B100 (ApoB100) minimal low density lipoprotein
      (LDL) receptor (LDLR) binding domain, residues
      3359-3369 of apolipoprotein B100 (ApoB100)

<400> SEQUENCE: 1

Arg Leu Thr Arg Lys Arg Gly Leu Lys
 1               5

<210> SEQ ID NO 2
<211> LENGTH: 18
<212> TYPE: PRT
<213> ORGANISM: Artificial Sequence
<220> FEATURE:
<223> OTHER INFORMATION: Description of Artificial Sequence:synthetic
      18A Segrest peptide, synthetic 18 amino acid class A amphipathic
      alpha-helix

<400> SEQUENCE: 2

Asp Trp Leu Lys Ala Phe Tyr Asp Lys Val Ala Glu Lys Leu Lys Glu
 1               5                  10                  15

Ala Phe

<210> SEQ ID NO 3
<211> LENGTH: 29
<212> TYPE: PRT
<213> ORGANISM: Artificial Sequence
<220> FEATURE:
<223> OTHER INFORMATION: Description of Artificial Sequence:synthetic
      18A chimeric Segrest peptide, synthetic 18A chimeric peptide
      (class A motif), ApoB100 LDLR binding domain flanked at N-
      terminal with 18A peptide, Peptide 1

<400> SEQUENCE: 3

Asp Trp Leu Lys Ala Phe Tyr Asp Lys Val Ala Glu Lys Leu Lys Glu
 1               5                  10                  15

Ala Phe Arg Leu Thr Arg Lys Arg Gly Leu Lys Leu Ala
            20                  25
```

```
<210> SEQ ID NO 4
<211> LENGTH: 29
<212> TYPE: PRT
<213> ORGANISM: Artificial Sequence
<220> FEATURE:
<223> OTHER INFORMATION: Description of Artificial Sequence:synthetic
      4F 18PA chimeric peptide (F3, F14), 18A chimeric Segrest peptide
      modified to contain four Phe, substitutions of F3 and F14 coupled
      to ApoB100 LDLR binding domain at N-terminal end

<400> SEQUENCE: 4

Asp Trp Phe Lys Ala Phe Tyr Asp Lys Val Ala Glu Lys Phe Lys Glu
 1               5                  10                  15

Ala Phe Arg Leu Thr Arg Lys Arg Gly Leu Lys Leu Ala
             20                  25

<210> SEQ ID NO 5
<211> LENGTH: 22
<212> TYPE: PRT
<213> ORGANISM: Artificial Sequence
<220> FEATURE:
<223> OTHER INFORMATION: Description of Artificial Sequence:synthetic
      B-peptide, apolipoprotein B100 (ApoB100) low density lipoprotein
      (LDL) receptor (LDLR) binding domain, residues 3352-3374, contains
      native protein N- and C-terminal flanking regions

<400> SEQUENCE: 5

Tyr Lys Leu Glu Gly Thr Thr Arg Leu Thr Arg Lys Arg Gly Leu Lys
 1               5                  10                  15

Leu Ala Thr Ala Leu Ser
             20

<210> SEQ ID NO 6
<211> LENGTH: 22
<212> TYPE: PRT
<213> ORGANISM: Artificial Sequence
<220> FEATURE:
<223> OTHER INFORMATION: Description of Artificial Sequence:synthetic
      11-A chimeric peptide, ApoA-1 helix 9 (11-A) chimeric peptide,
      amphipathic alpha-helix 9 of apolipoprotein A-1 (Apo-A1) coupled
      to ApoB100 LDLR binding domain

<400> SEQUENCE: 6

Pro Ala Leu Glu Asp Leu Arg Gln Gly Leu Leu Pro Arg Leu Thr Arg
 1               5                  10                  15

Lys Arg Gly Leu Lys Leu
             20

<210> SEQ ID NO 7
<211> LENGTH: 47
<212> TYPE: PRT
<213> ORGANISM: Artificial Sequence
<220> FEATURE:
<223> OTHER INFORMATION: Description of Artificial Sequence:synthetic
      18A-P-LDLR-P-18A chimeric peptide, two 18A Segrest peptides
      coupled before and after ApoB100 LDLR binding domain with Pro
      inserted before and after binding domain, Peptide 2

<400> SEQUENCE: 7

Asp Trp Leu Lys Ala Phe Tyr Asp Lys Val Ala Glu Lys Leu Lys Glu
 1               5                  10                  15

Ala Phe Pro Arg Leu Thr Arg Lys Arg Gly Leu Lys Pro Asp Trp Leu
             20                  25                  30

Lys Ala Phe Tyr Asp Lys Val Ala Glu Lys Leu Lys Glu Ala Phe
         35                  40                  45
```

```
<210> SEQ ID NO 8
<211> LENGTH: 40
<212> TYPE: PRT
<213> ORGANISM: Artificial Sequence
<220> FEATURE:
<223> OTHER INFORMATION: Description of Artificial Sequence:18A-LDLR
      chimeric peptide including LDLR flanking sequences, synthetic
      chimeric ApoB100 LDLR binding domain with native N- and C-
      terminal flanking sequences coupled to N-terminal 18A Segrest
      peptide, Peptide 3

<400> SEQUENCE: 8

Asp Trp Leu Lys Ala Phe Tyr Asp Lys Val Ala Glu Lys Leu Lys Glu
 1               5                  10                  15

Ala Phe Tyr Lys Leu Glu Gly Thr Thr Arg Leu Thr Arg Lys Arg Gly
            20                  25                  30

Leu Lys Leu Ala Thr Ala Leu Ser
        35                  40

<210> SEQ ID NO 9
<211> LENGTH: 89
<212> TYPE: PRT
<213> ORGANISM: Artificial Sequence
<220> FEATURE:
<223> OTHER INFORMATION: Description of Artificial Sequence:synthetic
      chimeric peptide with amphipathic alpha-helix and
      LDLR binding domain
<220> FEATURE:
<221> NAME/KEY: MOD_RES
<222> LOCATION: (1)..(40)
<223> OTHER INFORMATION: Xaa = naturally occuring amino acid or amino
      acid mimetic, may be present or absent
<220> FEATURE:
<221> NAME/KEY: MOD_RES
<222> LOCATION: (50)..(89)
<223> OTHER INFORMATION: Xaa = naturally occuring amino acid or amino
      acid mimetic, may be present or absent

<400> SEQUENCE: 9

Xaa Xaa Xaa Xaa Xaa Xaa Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Arg Leu Thr Arg Lys Arg Gly Leu
        35                  40                  45

Lys Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa
                85

<210> SEQ ID NO 10
<211> LENGTH: 18
<212> TYPE: PRT
<213> ORGANISM: Artificial Sequence
<220> FEATURE:
<223> OTHER INFORMATION: Description of Artificial Sequence:4F 18PA
      peptide (F3, F14), 18A chimeric Segrest peptide modified to
      contain four Phe, substitutions of F3 and F14, 1-R sequence in
      chimeric peptide

<400> SEQUENCE: 10

Asp Trp Phe Lys Ala Phe Tyr Asp Lys Val Ala Glu Lys Phe Lys Glu
 1               5                  10                  15

Ala Phe
```

```
<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence:
      apolipoprotein B100 (ApoB100) minimal low density lipoprotein
      (LDL) receptor (LDLR) binding domain native N-terminal flanking
      sequence, 1-R sequence in chimeric peptide

<400> SEQUENCE: 11

Tyr Lys Leu Glu Gly Thr Thr
 1               5

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence:
      apolipoprotein B100 (ApoB100) minimal low density lipoprotein
      (LDL) receptor (LDLR) binding domain native C-terminal flanking
      sequence, 2-R sequence in chimeric peptide

<400> SEQUENCE: 12

Leu Ala Thr Ala Leu Ser
 1               5

<210> SEQ ID NO 13
<211> LENGTH: 12
<212> TYPE: PRT
<213> ORGANISM: Artificial Sequence
<220> FEATURE:
<223> OTHER INFORMATION: Description of Artificial Sequence:11-A
      peptide helix 9 of apolipoprotein A-1 (Apo-A1) amphipathic alpha-
      helix plus Pro, 1-R sequence in chimeric peptide

<400> SEQUENCE: 13

Pro Ala Leu Glu Asp Leu Arg Gln Gly Leu Leu Pro
 1               5                  10

<210> SEQ ID NO 14
<211> LENGTH: 19
<212> TYPE: PRT
<213> ORGANISM: Artificial Sequence
<220> FEATURE:
<223> OTHER INFORMATION: Description of Artificial Sequence:18A Segrest
      peptide with Pro inserted after, 1-R sequence in chimeric
      peptide

<400> SEQUENCE: 14

Asp Trp Leu Lys Ala Phe Tyr Asp Lys Val Ala Glu Lys Leu Lys Glu
 1               5                  10                  15

Ala Phe Pro

<210> SEQ ID NO 15
<211> LENGTH: 19
<212> TYPE: PRT
<213> ORGANISM: Artificial Sequence
<220> FEATURE:
<223> OTHER INFORMATION: Description of Artificial Sequence:18A Segrest
      peptide with Pro inserted before, 2-R sequence in chimeric
      peptide

<400> SEQUENCE: 15

Pro Asp Trp Leu Lys Ala Phe Tyr Asp Lys Val Ala Glu Lys Leu Lys
 1               5                  10                  15

Glu Ala Phe
```

```
<210> SEQ ID NO 16
<211> LENGTH: 25
<212> TYPE: PRT
<213> ORGANISM: Artificial Sequence
<220> FEATURE:
<223> OTHER INFORMATION: Description of Artificial Sequence:18A Segrest
      peptide including apolipoprotein B100 (ApoB100) minimal low
      density lipoprotein (LDL) receptor (LDLR) binding domain native
      N-terminal flanking sequence, 1-R sequence in chimeric peptide

<400> SEQUENCE: 16

Asp Trp Leu Lys Ala Phe Tyr Asp Lys Val Ala Glu Lys Leu Lys Glu
1               5                   10                  15

Ala Phe Tyr Lys Leu Glu Gly Thr Thr
            20                  25
```